United States Patent
Spallitta

(10) Patent No.: US 10,500,183 B2
(45) Date of Patent: Dec. 10, 2019

(54) ACETYLCHOLINESTERASE INHIBITORS FOR TREATMENT OF DERMATOLOGICAL CONDITIONS

(71) Applicant: Attillaps Holdings, Denver, CO (US)

(72) Inventor: Frank Anthony Spallitta, Denver, CO (US)

(73) Assignee: Attillaps Holdings, Denver, CO (US)

( * ) Notice: Subject to any disclaimer, the term of this patent is extended or adjusted under 35 U.S.C. 154(b) by 0 days.

(21) Appl. No.: 15/319,897

(22) PCT Filed: Jun. 18, 2015

(86) PCT No.: PCT/US2015/036448
§ 371 (c)(1),
(2) Date: Dec. 19, 2016

(87) PCT Pub. No.: WO2015/195928
PCT Pub. Date: Dec. 23, 2015

(65) Prior Publication Data
US 2017/0135978 A1 May 18, 2017

Related U.S. Application Data

(60) Provisional application No. 62/014,520, filed on Jun. 19, 2014.

(51) Int. Cl.
| | | |
|---|---|---|
| *A61K 31/27* | (2006.01) | |
| *A61K 9/00* | (2006.01) | |
| *A61K 9/02* | (2006.01) | |
| *A61K 9/20* | (2006.01) | |
| *A61K 9/48* | (2006.01) | |
| *A61K 31/683* | (2006.01) | |
| *A61K 36/185* | (2006.01) | |
| *A61K 36/324* | (2006.01) | |

(52) U.S. Cl.
CPC ............ *A61K 31/27* (2013.01); *A61K 9/0075* (2013.01); *A61K 9/02* (2013.01); *A61K 9/2009* (2013.01); *A61K 9/2013* (2013.01); *A61K 9/2054* (2013.01); *A61K 9/4825* (2013.01); *A61K 9/4858* (2013.01); *A61K 9/4866* (2013.01); *A61K 31/683* (2013.01); *A61K 36/185* (2013.01); *A61K 36/324* (2013.01)

(58) Field of Classification Search
CPC ...................................................... A61K 31/27
See application file for complete search history.

(56) References Cited

U.S. PATENT DOCUMENTS

| | | | |
|---|---|---|---|
| 5,629,300 A | 5/1997 | Boberg et al. | |
| 5,952,372 A * | 9/1999 | McDaniel | A61K 31/35 514/453 |
| 6,133,310 A | 10/2000 | Parks | |
| 6,258,378 B1 | 7/2001 | Schneider et al. | |
| 6,406,713 B1 | 6/2002 | Janoff et al. | |
| 7,919,522 B2 | 4/2011 | Soll et al. | |
| 8,440,240 B2 | 5/2013 | Gao et al. | |
| 8,475,818 B2 | 7/2013 | Guerino et al. | |
| 8,546,357 B2 | 10/2013 | Akama et al. | |
| 2003/0040504 A1 | 2/2003 | Gans et al. | |
| 2005/0143325 A1* | 6/2005 | Guzzo | A01N 43/90 514/28 |
| 2005/0256028 A1* | 11/2005 | Yun | A61K 31/137 332/128 |
| 2006/0084632 A1* | 4/2006 | Goyal | A01N 25/04 514/65 |
| 2007/0020304 A1 | 1/2007 | Tamarkin et al. | |
| 2007/0287733 A1* | 12/2007 | Snorrason | A61K 31/27 514/319 |
| 2008/0292560 A1 | 11/2008 | Tamarkin et al. | |
| 2008/0299220 A1 | 12/2008 | Tamarkin et al. | |
| 2009/0068255 A1 | 3/2009 | Yu et al. | |
| 2009/0099135 A1 | 4/2009 | Enan | |
| 2009/0214676 A1* | 8/2009 | Gao | A61K 36/23 424/725 |
| 2010/0099668 A1 | 4/2010 | Guerino et al. | |
| 2010/0333221 A1 | 12/2010 | Chabriere et al. | |

(Continued)

FOREIGN PATENT DOCUMENTS

| | | |
|---|---|---|
| EP | 2355790 A2 | 8/2011 |
| GB | 2419093 A | 4/2006 |

(Continued)

OTHER PUBLICATIONS

Jarmuda S. et al. Potenitial Role of Demodex Mites and Bacteria in the Induction of Rosacea. J of Medical Microbiology 61:1504-1510, 2012. (Year: 2012).*
Rather P. et al. Human Demodex Mite: The Versatile Mite of Dermatological Importance. Indian J of Dermatology 59(1)60-66, Jan.-Feb. 2014.*
Pohanka, M. Acetylcholinesterase Inhibitors: A Patent Review 2008-Present. Expert Opinion on Therapeutic Patents 22:8, 871-886, Jul. 2012.*
Agres "New Life for Old Drugs" *Advantage Business Media*, [Accessible on the Internet at: http://www.dddmag.com/articles/2011/07/new-life-old-drugs] (Sep. 29, 2011).
Akilov "Immune response in demodicosis", *J. Eur. Acad. Dermatol. Venereol.*, 18(4):440-4 (2004).
Akilov et al., "Association between human demodicosis and HLA class I", *Clin. Exp. Dermatol.*, 28(1):70-3 (2003).

(Continued)

*Primary Examiner* — Ralph J Gitomer
(74) *Attorney, Agent, or Firm* — Leydig, Voit & Mayer, Ltd.

(57) ABSTRACT

Embodiments of the invention involve treating skin afflictions by the topical or oral use of acetylcholinesterase inhibitor. By effectively reducing or eliminating the population of *Demodex* mites in affected skin areas and areas where *Demodex* mites may exist, this treatment achieves a more complete remission of clinical signs and symptoms of the skin afflictions than any previously described method. Embodiments of the invention are useful for treating skin afflictions including common acne, seborrheic dermatitis, perioral dermatitis, an acneform rash, transient acantholytic dermatosis, acne necrotica milliaris, psoriasis, steroid induced dermatitis, primary irritation dermatitis and rosacea.

29 Claims, No Drawings

(56) References Cited

U.S. PATENT DOCUMENTS

| | | | |
|---|---|---|---|
| 2011/0009457 A1 | 1/2011 | Gorgens et al. | |
| 2011/0033395 A1 | 2/2011 | Kaoukhov et al. | |
| 2011/0034471 A1 | 2/2011 | Held | |
| 2011/0059988 A1 | 3/2011 | Heckeroth et al. | |
| 2011/0150795 A1 | 6/2011 | Loing et al. | |
| 2011/0288141 A1 | 11/2011 | Freehauf et al. | |
| 2013/0095051 A1 | 4/2013 | Kaoukhov et al. | |
| 2013/0131016 A1 | 5/2013 | Akama et al. | |
| 2013/0131017 A1 | 5/2013 | Akama et al. | |
| 2013/0131050 A1 | 5/2013 | Matsunaga et al. | |
| 2013/0177662 A1* | 7/2013 | Msika | A61K 8/645 |
| | | | 424/757 |
| 2013/0225516 A1 | 8/2013 | Soll et al. | |
| 2013/0243886 A1 | 9/2013 | Hu et al. | |
| 2013/0338197 A1 | 12/2013 | Mita et al. | |
| 2013/0344128 A1* | 12/2013 | Gao | A61K 36/23 |
| | | | 424/443 |
| 2014/0017216 A1 | 1/2014 | Klein et al. | |
| 2015/0086596 A1* | 3/2015 | Spallitta | A01N 57/12 |
| | | | 424/407 |

FOREIGN PATENT DOCUMENTS

| | | |
|---|---|---|
| WO | WO 2004/000337 A1 | 12/2003 |
| WO | WO 2009/010754 A2 | 1/2009 |
| WO | WO 2009/030686 A1 | 3/2009 |
| WO | WO 2010/066639 A2 | 6/2010 |
| WO | WO 2013/078071 A1 | 5/2013 |
| WO | WO 2015/017328 A2 | 2/2015 |
| WO | WO 2015/195928 A1 | 12/2015 |

OTHER PUBLICATIONS

Akilov et al., "A clinico-pathological approach to the classification of human demodicosis", *J. Dtsch Dermatol Ges.*, 3(8):607-14 (2005).
Askin et al., "Comparison of the two techniques for measurement of the density of Demodex folliculorum: standardized skin surface biopsy and direct microscopic examination", *Br. J. Dermatol.*, 162(5):1124-6 (2010).
Assen et al., "Ivermectin: pharmacology and application in dermatology", *International J. of Dermatology*, 44(12):981-988 (2005).
Aycan et al., "Frequency of the appearance of *Demodex* sp. in various patient and age groups", *Turkiye Parazitoloji Dergisi.* 31(2):115-8 (2007).
Ayres, Jr. "Rosaceam Like Demodicidosis", *Calif Med.*, 98(6):328-330 (1963).
Baima et al., "Demodicidosis revisited", *Acta Derm Venereol.*, 82(1):3-6 (2002).
Banker et al., "Disperse Systems", *Modern Pharmaceutics*, Ch. 9, Marcel Dekker, Inc. New York, New York (1979).
Banker et al., "Tablet Dosage Forms", *Modern Pharmaceutics*, Ch. 10, Marcel Dekker, Inc. New York, New York (1979).
Barnett, "That Rose in Your Cheeks Could Be Bacteria," ABC News Medical Unit, [Accessible on the Internet at: http://abcnews.go.com/blogs/health/2012/08/29/that-rose-in-your-cheeks-could-be-bacteria] (Aug. 29, 2012).
Basta-Juzbasić et al., "Demodex folliculorum in development of dermatitis rosaceiformis steroidica and rosacea-related diseases", *Clin Dermatol.*, 20(2):135- 40 (2002).
Beridze et al., "Cryotherapy in treatment of skin demodecosis", *Georgian Med. News*, (170):43-5 (2009).
Bhatia et al., "Dispelling the Mystery of Demodex", *The Dermatologist*, 15(1):38-41 (2006).
Bikowski et al., "Demodex Dermatitis A Retrospective Analysis of Clinical Diagnosis and Successful Treatment with Topical Crotamiton", *J. Clin Aesthet Dermatol.*, 2(1):20-5 (2009).
Bonnar et al., "The Demodex mite population in rosacea", *J. Am Acad Dermatol.* 28(3):443-8 (1993).
Borgo et al., "PCR analysis for Wolbachia in human and canine Demodex mites", *Arch Dermatol Res.*, 301(10):747-52 (2009).
Casas et al., "Quantification of Demodex folliculorum by PCR in rosacea and its relationship to skin innate immune activation", *Exp Dermatol.*, 21:906-910 (2012).
Castillo, "Red skin condition rosacea may be due to bacteria in skin mites," CBS News. [Accessible on the Internet at http://www.cbsnews.com/8301-504763_162-57503771-10391704/red-skin-condition-rosacea-may-be-due-to-bacteria-in-skin-mites] (Aug. 30, 2012).
Crawford et al., "Rosacea: I. Etiology, pathogenesis, and subtype classification", *J. Am Acad Dermatol.*, 51(3):327-41 (2004).
Cresce et al., "The Quality of Life Impact of Acne and Rosacea Compared to Other Major Medical Conditions", *J. Drugs Dermatol.*, 13(6):692-7 (2014).
Czepita et al., "Investigations on the occurrence as well as the role of Demodex follicuforum and Demodex brevis in the pathogensis of blepharitis," *Klin Oczna*. 107(1-3):80-2 (2005).
Czepita et al., "Demoodex folliculorum and Demodex brevis as a cause of chronic marginal blepharitis", *Ann Acad Med Stetin.*, 53(1):63-7 (2007).
Del Rosso et al., "An Evaluation of the Potential Correlations Between Pathophysiologic Mechanisms, Clinical Manifestaions, and Managemant of Rosacea", *Cutis.*, 91(3 Suppl):1-8 (2013).
Demmler, "Blepharitis. Demodex folliculorum, associated pathogen spectrum and specific therapy," *Ophthalmologe*. 94(3):191-6 (1997).
Dittrich, "Synergistic Effect Between Vapors of C-8514/Schering 36268 and Dichlorvos Against the Carmine Spider Mite", 59(4):893-896 (1966).
Dolenc-Voljc et al., "Density of Demodex folliculorum in perioral dermatitis", *Acta Derm Venereol.*, 85(3):211-5 (2005).
Efi Pasmatzi et al., "Rosacea-Like Demodicosis Induced by Topical Pimecrolimus: Immunohistochemical Evaluation of Inflammatory Infiltrate", *Hospital Chronicles*, 4(4):172-174 (2009).
Elston, "Demodex mites: Facts and controversies", *Clin Dermatol*, 28(5):502-504 (2010).
Erbagci et al., "The significance of Demodex folliculorum density in rosacea", *Int. J. Dermatol.*, 37(6):421-5 (1998).
Fell, "Demodex Folliculorum in Diseased Conditions of the Human Face", *Proceedings of the Ninth Annual Meeting of the American Society of Microscopists*, 8:120-127 (1886).
Forstinger et al., "Treatment of rosacea-like demodicidosis with oral ivermectin and topical permethrin cream" *J. Am. Acad. Dermatol.*, 41(5 Pt 1):775-7 (1999).
Forton, "Demodex-associated folliculitis", *Am. J. Dermatopathol.* 20(5):536-7 (1998).
Forton, "Standardized skin surface biopsy: method to estimate the Demodex folliculorum density, not to study the Demodex folliculorum prevalence", *J. Eur. Acad. Dermatol. Venereol.*, 21(9):1301-2 (2007).
Forton, "Papulopustular rosacea, skin immunity and Demodex: pityriasis folliculorum as a missing link," *J. Eur. Acad. Dermatol. Venereol.*, 26(1):19-28. (2011).
Forton et al., "Density of Demodex folliculorum in rosacea: a case-control study using standardized skin-surface biopsy", *Br. J. Dermatol.*, 128:650-9 (1993).
Forton et al., "Demodex folliculorum and topical treatment: acaricidal action evaluated by standardized skin surface biopsy", *Br. J. Dermatol.*, 138(3):461-6. (1998).
Forton et al., "Limitations of standardized skin surface biopsy in measurement of the density of Demodex folliculorum. A case report", *Br. J. Dermatol.*, 139(4):697-700 (1998).
Forton et al., "Demodicosis and rosacea: epidemiology and significance in daily dermatologic practice", *J. Am. Acad. Dermatol.*, 52(1):74-87 (2005).
Fulk et al., "Pilocarpine gel for the treatment of demodicosis—a case series", *Optom. Vis. Sci.*, 73(12):742-5 (1996).
Gao et al., "In vitro and in vivo killing of ocular Demodex by tea tree oil", *Br. J. Ophthalmol.*, 89(11):1468-73 (2005).
Gao et al., "Clinical treatment of ocular demodecosis by lid scrub with tea tree oil", *Cornea*, 26(2):136-43 (2007).

(56) References Cited

OTHER PUBLICATIONS

Georgala et al., "Increased density of Demodex folliculorum and evidence of delayed hypersensitivity reaction in subjects with papulopustular rosacea", *J. Eur. Acad. Dermatol. Venereol.*,15(5):441-4 (2001).
Gillette, "Bacteria-laden mites may cause rosacea," Dermatology Times, [Accessible on the Internet at: http://dermatologytimes.modernmedicine.com/dermatology-times/content/bacteria-laden-mites-may-cause-rosacea] (Sep. 5, 2012).
Goodman, "Are Mites Causing Your Rosacea?," WebMD, LLC, [Accessible on the Internet at: http://www.webmd.com/skin-problems-and-treatments/news/20120830/are-mites-causing-your-rosacea] (Aug. 30, 2012).
Hom et al., "Demodex", *Optom. Vis. Sci.*, 90(7):e198-205. (2013).
Hsu et al., "Demodicosis: a clinicopathological study", *J. Am. Acad. Dermatol.*, 60(3):453-62 (2009).
Ivanhoe Newswire, "Something to Blush About, Medical Breakthroughs", *Ivanhoe Newswire* (Dec. 11, 2007).
Ivy, "Demodicidosis in childhood acute lymphoblastic leukemia; an opportunistic infection occurring with immunosuppression", *J. of Pediatrics*, 127(5):751-4 (1995).
Jansen et al., "Rosacea-like demodicidosis associated with acquired immunodeficiency syndrome", 144(1):139-42 (2001).
Jarmuda et al., "Potential role of Demodex mites and bacteria in the induction of rosacea", *J. of Medical Microbiology*, 61(11):1504-1510 (2012).
Jesitus, "Empirical treatment is key to identifying rosacea, other dermatoses", *Dermatology Times* (2007).
Jio, "Health & Beauty: Could These Tiny Mites Be Causing Your Rosacea?" *Conde Nast*, [Accessible on the Internet at: http://www.glamour.com/health-fitness/blogs/vitamin-g/2012/08/health-beauty-could-these-tiny] (Aug. 31, 2012).
Kennedy, "CollaGenex wins FDA approval for Oracea", *MarketWatch, Inc.*, [Accessible on the Internet at: http://www.marketwatch.com/story/collagenex-wins-fda-approval-for-oracea] (2006).
Kheirkhah et al., "Corneal manifestations of ocular demodex infestation", *Am. J. Ophthalmol.*, 143(5):743-749 (2007).
Kligman et al., "Demodex folliculorum: Requirements for Understanding Its Role in Human Skin Disease", *J. of Investigative Dermatology*, 131:8-10 (2011).
Kulac et al., "Clinical importance of Demodex folliculorum in patients receiving phototherapy", *Int. J. Dermatol.*, 47(1):72-7 (2008).
Kupiec-Banasikowska et al., "Rosacea", WebMD, LLC, [Accessible on the Internet at: http://emedicine.medscape.com/article/1071429-overview] (2007).
Lacey et al., "Mite-related bacterial antigens stimulate inflammatory cells in rosacea", *Br. J. Dermatol.*, 157(3):474-81 (2007).
Lacey et al., "Under the lash: Demodex mites in human diseases", *Biochem.(Lond)*, 31(4):2-6 (2009).—Author manuscript provided.
Lacey et al., "Demodex quantification methods: Limitations of Confocal Laser Scanning Microscopy (CLSM)", *Br. J. Dermatol.*, 169(1):212-3 (2013).
Larios et al., "Rosacea-like demodicidosis," *Lancet Infect Dis.*, 8(12):804 (2008).
Lazaridou et al., "The potential role of microorganisms in the development of rosacea", *J. of the German Society of Dermatology*, 9:21-25 (2010).
Lee et al., "Granulomatous rosacea-like demodicidos", *Dermatol. Online J.*, 13(4):9 (2007).
Li et al., "Correlation between ocular Demodex infestation and serum immunoreactivity to Bacillus proteins in patients with Facial rosacea", *Ophthalmology*, 117(5):870-877 (2010).
Liu et al., "Pathogenic role of Demodex mites in blepharitis," *Curr Opin Allergy Clin Immunol.* 10(5):505-510 (2010).
Mackenzie "Rosacea may be caused by mite feces in your pores," *New Scientist*, [Accessible on the Internet at: https://www.newscientist.com/article/dn22227-rosacea-may-be-caused-by-mite-faeces-in-your-pores/] (Aug. 30, 2012).

Manolette et al., "Demodicosis", *WebMD, LLC*, [Accessible on the Internet at URL: http://emedicine.medscape.com/article/1203895-overview] (Nov. 5, 2015). Haddon W F, M I Mancini, M Mclaren, A Effio, L A Harden, R I Egre, & J L Bradford (1994). Cereal Chemistry 71 (2): 207-215.
Mccarty, "Bayer Sues Glenmark Over Patent for Rosacea Drug Finacea," *Bloomberg L. P.* [Accessible on the Internet at URL: http://www.bloomberg.com/news/articles/2013-03-15/bayer-sues-glenmark-over-patent-for-rosacea-drug-finacea] (Mar. 15, 2013).
Moore, "Rosacea May Be Caused by Bacteria Released by Tiny Mites Living on the Skin," *Medical News Today*, [Accessible on the Internet at: http://www.medicalnewstoday.com/releases/249664.php] (Aug. 31, 2012).
Moravvej et al., "Association of rosacea with demodicosis", *Arch, Iran Med.*, 10(2):199-203 (2007).
Mumcuoglu et al., "The role of HLA A2 and Cw2 in the pathogenesis of human demodicosis", *Dermatology*, 210(2):109-14 (2005).
National Rosacea Society, "Mites and Eye Symptoms," NRS Web Blog Thursday. [Accessible on the Internet at: http://www.rosacea.org/weblog/mites_and_eye_symptoms] (2010).
National Rosacea Society, "All About Rosacea," *National Rosacea Society*, [Accessible on the Internet at: http://www.rosacea.org/patients/allaboutrosacea.php] (2016).
National Rosacea Society, "NRS-Funded Studies Advance Knowledge of Rosacea's Causes," *Rosacea Review*, [Accessible on the Internet at: http://www.rosacea.org/rr/2010/fall/article_1.php] (Fall 2010).
National Rosacea Society, "New Study Shows Role for Bacteria in Development of Rosacea Symptoms," *NRS Press Release*. [Accessible on the Internet at: http://www.rosacea.org/press/archive/20040503.php] (May 3, 2004).
National Rosacea Society, "The Chicken, not the Egg?" *National Rosacea Society*, [Accessible on the Internet at: http://www.rosacea.org/weblog/the_chicken_not_the_egg] (Sep. 5, 2012).
NBC News, "Tiny mites on your face may cause rosacea," *NBC News*, [Accessible on the Internet at URL: http://vitals.nbcnews.com/_news/2012/08/29/13554038-tiny-mites-on-your-face-may-cause-rosacea?lite] (Aug. 29, 2012).
New York Daily News, "New discovery may hold clues to rosacea cure; Red bumps may be linked to mites living on the face," New York Daily News. [Accessible on the Internet at: http://www.nydailynews.com/life-style/health/new-discovery-hold-clues-rosacea-cure-red-bumps-linked-mites-living-face-article-1.1152511] (Sep. 5, 2012).
Nielsen et al., "Glycolamide esters as biolabile prodrugs of carboxylic acid agents: synthesis, stability, bioconversion, and physicochemical properties", *J. of Pharmaceutical Sciences*, 77:285-298 (1988).
NIH News, "Lavender and Tea Tree Oils May Cause Breast Growth in Boys," *NIH News* [Accessible on the Internet at: http://www.nih.gov/news-events/news-releases/lavender-tea-tree-oils-may-cause-breast-growth-boys] (2007).
Norn, "Demodex folliculorum. Incidence and possible pathogenic role in the human eyelid", *Acta Ophthalmologica*, Ch. VII, In, 48(S108):71-78 (1970).
O'Connell, "Study finds cause of rosacea," *The Irish Times* [Accessible on the Internet a: http://www.irishtimes.com/news/health/study-finds-cause-of-rosacea-1.699476] (Jul. 14, 2009).
O'Reilly et al., "Demodex-associated bacterial proteins induce neutrophil activation", *Br. J. Dermatol.*, 166(4):753-60. (2011).
O'Reilly et al., "Demodex-associated Bacillus proteins induce an aberrant wound healing response in a corneal epithelial cell line (hTCEpi)", *Invest. Ophthalmol. Vis. Sci.* 53(6):3250-9 (2012).
O'Reilly et al., "Positive correlation between serum immunoreactivity to Demodex-associated Bacillus proteins and erythematotelangiectatic rosacea", *Br. J. Dermatol.*, 167(5):1032-6. (2012).
Pena et al., "Is demodex really non-pathogenic?", *Rev Inst Med Trop Sao Paulo*, 42(3):171-3 (2000).
Pitman, "Researchers Claim to be Closer Towards Effective Treatment of Rosacea Cosmetics Design," *William Reed Business Media SAS* [http://www.cosmeticsdesign.com/Formulation-Science/Researchers-claim-to-be-closer-towards-effective-treatment-of-rosacea] (Aug. 30, 2012).

(56) References Cited

OTHER PUBLICATIONS

Press Trust of India, "Rosacea may be caused by skin bacteria: study," Business Standard, [Accessible on the Internet at: http://www.business-standard.com/article/pti-stories/rosacea-may-be-caused-by-skin-bacteria-study-112083000384_1.html] (Aug. 30, 2012).
Prieto et al., "Effects of intense pulsed light on sun-damaged human skin, routine, and ultrastructural analysis", Lasers Surg. Med., 30(2):82-5(2002).
Psmicrographs "Follicle mite (Demodex folliculorum)," PSmicrographs [Accessible on the Internet at: www.psmicrographs.co.uk/follicle-mite--demodex-folliculorum-/science-image/80016342].
Rebora, "The management of rosacea", Am. J. Clin. Dermatol. 3(7):489-96 (2002).
Ríos-Yuil et al., "Evaluation of Demodex folliculorum as a Risk Factor for the Diagnosis of Rosacea in Skin Biopsies. Mexico's General Hospital (1975-2010)", Indian J Dermatol., 58(2):157. pp. 1-10 (2013).
Roihu et al., "Demodex mites in acne rosacea", J. Cutan Pathol., 25(10):550-2. (1998).
Román-Curto et al., "Demodicidosis simulating acute graft-versus-host disease after allogeneic stem cell transplantation in one patient with acute lymphoblastic leukemia", Transpl. Infect. Dis., 14:387-390 (2012).
Rufli et al., "The hair follicle mites Demodex folliculorum and Demodex brevis: biology and medical importance. A review", Dermatologica. 162(1):1-11 (1981).
Sahn et al., "Demodicidosis in a child with leukemia", J. Am. Acad. Dermatol., 27(5 Pt 2):799-801 (1992).
Sandoz, "Sandoz Launches First Generic Version of Metrogel® 1% in the US," Sandoz: A Novartis [Accessible on the Internet at: http://www.sandoz.com/media_center/press_releases_news/global_news/sandoz_launches_first_generic_version_of_metrogel_reg_1_in_the_us.shtml].
Sattler et al., "Non-invasive in vivo detection and quantification of Demodex mites by confocal laser scanning microscopy", Br. J. Dermatol., 167(5):1042-7 2012).
Schaller et al., "Demodex abscesses: clinical and therapeutic challenges", J. Am. Acad Dermatol., 49(5 Suppl):S272-4 (2003).
Schmidt et al., "Demodex and rosacea, III: Treatment of Demodex mites associated with inflammatory rosacea", Cosmetic Dermatology, 17(10):655-658 (2004).
Schneider et al., "Metrifonate: A Cholinesterase Inhibitor for Alzheimer's Disease Therapy", CNS Drug Reviews, 5(1):13-26 (1999).
Science Daily, "Bacterial Cause Found for Skin Condition Rosacea," Science Daily [Accessible on the Internet at URL: https://www.sciencedaily.com/releases/2012/08/120829195121.htm] (Aug. 29, 2012).
Sekizawa et al., "Environmental Health Criteria 79: Dichlorvos", World Health Organization. Geneva, Switzerland (1989).
Shelley et al., "Unilateral demodectic rosacea", J. Am. Acad Dermatol., 20(5 Pt 2):915-7 (1989).
Sifferlin "Rosacea: Caused by Mite Poop in Your Facial Pores?" Time Magazine. [Accessible on the Internet at: http://healthland.time.com/2012/09/04/rosacea-caused-by-mite-poop-in-your-facial-pores/] (Sep. 4, 2012).
Spiegel et al., "Use of nonaqueous solvents in parenteral products", J. of Pharmaceutical Sciences, 52(10):917-927 (1963).
Stanisław et al., "The potential role of Demodex folliculorum mites and bacteria in the induction of rosacea," J. of Medical Microbiology, 61:1504-1510 (2012).
Talghini et al., "Demodex folliculorum and Skin Disease: A Case-Control Study", J. Med. Sci., 14(5):229-234 (2014).
Walton et al., "Studies in vitro on the relative efficacy of current acaricides for Sarcoptes scabiei var. hominis", Trans. Royal Chem. Soc., 94:92-96 (2000).
Wilkin et al., "Standard classification of rosacea: Report of the National Rosacea Society Expert Committee on the Classification and Staging of Rosacea", J. of the American Academy of Dermatology, 46:584-587(2002).
Wood "Compendium of Pesticide Common Names; Classification of acaricides," [Accessible on the Internet at: http://alanwood.net/pesticides/class_acaricides.html] pp. 1-8 (Archived web page from Dec. 12, 2010).
Woods, "It's Enough to Make Your Skin Crawl: Microscopic Mites May Be Linked to Acne, Thinning Hair and Other Skin Disorders," University of Florida's Institute of Food and Agricultural Sciences. [Accessible on the Internet at: http://entomology.ifas.ufl.edu/pestalert/acne.htm] (2003).
Wozniacka et al., "Topical application of 1-methylnicotinamide in the treatment of rosacea: a pilot study", Clin. Exp. Dermatol., 30(6):632-5 (2005).
Zahavi et al., "Sensitivity of acetylcholinesterase in spider mites to organo-phosphorus compounds", Biochemical Pharmacology, 19:219-225 (1970).
Zhao et al., "Retrospective analysis of the association between demodex infestation and rosacea", Arch. Dermatol. 146(8):896-902 (2010).
Zhao et al., "Facial dermatosis associated with Demodex: A case-control study", Journal of Zhejiang University-Science B. 12(12):1008-1015 (2011).
Zhao et al., "A meta-analysis of association between acne vulgaris and infestation", Journal of Zhejiang University-Science B. 13(3):192-202 (2012).
Zhao et al., "Influence of temperature and medium on viability of Demodex folliculorum and Demodex brevis", Exp. Appl. Acarol., 54:421-425 (2011).
International Search Report with Written Opinion corresponding to International Patent Application No. PCT/US2014/048420, dated Nov. 14, 2014, 19 pages.
International Search Report with Written Opinion corresponding to International Patent Application No. PCT/US2015/036448, dated Sep. 16, 2015, 18 pages.
Supplementary European Search Report corresponding to European Patent Application No. 14832600, dated Jun. 29, 2016, 11 pages.
Supplementary European Search Report corresponding to European Patent Application No. 15809417.7, dated Feb. 9, 2018, 5 pages.
U.S. Appl. No. 14/444,748, filed Jul. 28, 2014, Pending.

\* cited by examiner

ACETYLCHOLINESTERASE INHIBITORS FOR TREATMENT OF DERMATOLOGICAL CONDITIONS

CROSS-REFERENCE TO RELATED APPLICATIONS

This application claims the benefit of priority to U.S. Provisional Application No. 62/014,520 filed Jun. 19, 2014, which is hereby incorporated by reference in its entirety to the extent not inconsistent herewith.

BACKGROUND OF INVENTION

Provided herein are methods for treatment of various skin afflictions in humans employing topically applied or orally dosed acetylcholinesterase inhibitors and/or carbamates, such as ethyl carbamates to inactivate certain organisms associated with the skin affliction. For example, by reducing or eliminating *Demodex* organisms from affected skin areas, the methods reduce clinical signs of the skin afflictions which are primarily due to allergic and vasomotor responses of the body to the organism and bacteria that are carried by the organism.

Rosacea, originally termed acne rosacea, is a chronic inflammatory skin condition most commonly affecting the face and eyelids of middle-aged adults. Clinical signs include erythema (redness), dryness, papules, pustules, and nodules either singly or in combination in the involved skin areas. Eyelid involvement may be manifested by mild conjunctival irritation or inflammation of the meibomian (oil) glands on the eyelid margin. Chronic eyelid irritation can result in loss of eyelashes. No visual impairment accompanies the eyelid irritation. Chronic involvement of the nose with rosacea in men can cause a bulbous enlargement known as rhinophyma. In the classic situation, the condition develops in adults between the ages of 30 and 50. While certain lesions of rosacea may mimic lesions of acne vulgaris, the processes are separate and distinct, the principal differences being the presence of comedones (whiteheads and blackheads) only in acne vulgaris and not in rosacea, the characteristic midfacial localization and flushing of rosacea not seen in acne, and the potential for eyelid involvement in rosacea which never occurs in acne. In fact, the clinical observation has been made that persons who have classic acne vulgaris as teenagers rarely, if ever, develop full-blown rosacea as adults.

Rosacea develops in four stages over several years, in spasms aggravated by variations in temperature, alcohol, spices, exposure to sunlight and emotions. The various stages of the disease include:

Stage 1: stage of erythema episodes. The patients have erythrosis spasms due to the sudden dilation of the arterioles of the face, which then take on a congestive, red appearance. These spasms are caused by the emotions, meals and temperature changes.

Stage 2: stage of couperosis, i.e., of permanent erythema with telangiectasia. Certain patients also have oedema on the cheeks and the forehead.

Stage 3: inflammatory stage with appearance of inflammatory papules and pustules, but without affecting the sebaceous follicles and thus with absence of cysts and comedones.

Stage 4: rhinophyma stage. This late phase essentially affects men. The patients have a bumpy, voluminous red nose with sebaceous hyperplasia and fibrous reordering of the connective tissue.

The etiology of rosacea is still not fully understood, although many theories have been advanced. It has been a frequently discussed topic in medical circles but a full consensus has not been reached. The prominent presence of erythema (redness) and flushing of the face of affected persons with aggravation from heat, sunshine, and alcohol has focused attention on this aspect of the disease. A common hypothesis is based on the characteristic presence of the parasite *Demodex folliculorum* in the case of patients suffering from rosacea. This organism is absent in the other forms of acne such as common acne. Other factors have been described as possibly contributing towards the development of rosacea, such as hormonal factors and especially endocrine factors, climatic and immunological factors, and bacterial factors via the presence of *Helicobacter pylori*, a bacterium associated with gastrointestinal disorders.

Treatment with medications to block such vasomotor flushing has no effect on other aspects of the disease such as papules and pustules. Treatment with oral and topical antibiotics has been shown to effectively block progression of rosacea through a poorly understood anti-inflammatory mechanism or by destroying bacteria associated *Demodex folliculorum* mites, but studies have shown that these medications do not act by killing *Demodex folliculorum* organisms in affected skin. Antibiotics have to be continually administered and are in many cases only marginally effective. Many times patients cannot tolerate the side effects related to the oral antibiotics.

Although hypothesized as a root cause of rosacea, many rosacea subtypes and seborheic dermatitis, *demodex brevis* and *demodex folliculorum* has yet to reach consensus and no commercially viable pharmacological solutions are available for treating *demodex brevis* and *demodex folliculorum*. Democodosis presents like rosacea or seborheic dermatitis but is confirmed as being caused by *demodex* mites. Reaction to the presence or metabolic activity of *demodex* mites in facial follicles has been discussed as a cause of rosacea but previous studies where topical miticides other than acetylcholinesterase inhibitor have been used have shown inconsistent and marginal results.

In a National Rosacea Society funded study, the National University of Ireland, Maynooth, found that the bacterium *Bacillus oleronius* stimulated an immune system response, inducing high levels of T-cell proliferation, in 79 percent of patients with subtype 2 rosacea, compared with only 29 percent of patients without the disorder. T-cell proliferation induces an inflammatory response, evident as papules and pustules. This indicates that the *Bacillus* bacteria found in the *Demodex* mite produce an antigen that could be responsible for the tissue inflammation associated with papulopustular rosacea. Many current antibiotic treatments for rosacea are theorized to be effective based on their ability to effectively combat *Bacillus oleronius*.

Conventionally, rosacea is treated orally or topically with antibiotics such as tetracyclines, erythromycin or clindamycin, but also with vitamin A, salicylic acid, antifungal agents, steroids, anti-infectious agents such as benzoyl peroxide, or with isotretinoin in severe cases or most commonly with metronidazole (an antibacterial agent).

Metronidazole is known for its antiparasitic, antiprotozoan and antibacterial properties. It is especially used for treating *Helicobacter pylori* infections. It is also prescribed in the treatment of rosacea, for its advantageous properties on the inflammatory lesions of rosacea, specifically on papules and pustules. Metronidazole exerts selective toxicity towards anaerobic microorganisms and also hypoxic cells.

On the latter, metronidazole is reduced to various derivatives that are capable of changing the structure of their DNA.

U.S. Patent Application 2013/0095051A filed Dec. 6, 2012 describes a method of treating rosacea using avermectin/metronidazole in a topical application. U.S. Pat. No. 5,952,372 describes a method for treating rosacea using ivermectin orally or topically in order to reduce and eliminate the parasite *Demodex folliculorum* present on the skin of patients.

Ivermectin belongs to the avermectin family, a group of macrocyclic lactones produced by the bacterium *Streptomyces avermitilis*. The avermectins especially include ivermectin, invermectin, avermectin, abamectin, doramectin, eprinomectin and selamectin. Ivermectin is known in prior art for its antiparasitic and anthelmintic properties. The antiparasitic activity is thought to be due to the opening of a chlorine channel in the membrane of the neurons of the parasite under the effect of an increased release of the neuromediator GABA (gammaaminobutyric acid), inducing neuromuscular paralysis that may lead to the death of certain parasites. Ivermectin also interacts with other chlorine channels, especially those dependent on the neuromediator GABA (gammaaminobutyric acid).

Ivermectin is conventionally administered in the dermatological treatment of endoparasitic manifestations such as onchocerciasis and myiasis. U.S. Pat. No. 6,133,310 describes the use of ivermectin in the treatment of rosacea in order to reduce and eliminate the parasite *Demodex folliculorum* present on the skin of patients. U.S. Pat. No. 6,133,310 describes the use of ivermectin in the treatment of rosacea in order to reduce and eliminate the parasite *Demodex folliculorum* present on the skin of patients.

However, these treatments and compounds have drawbacks such as irritation and intolerance phenomena, especially when they are administered for a prolonged period. All current Rosacea treatments seem only to be suppressive and not curative, acting especially on the pustulous spasms occurring during the inflammatory stage.

According to the National Rosacea Society an estimated 16 million Americans have Rosacea, yet only a small fraction are being treated. Rosacea's etiology is currently under dispute in the dermatology community. Rosacea (roe-ZAY-she-uh) is a common skin condition that causes redness in your face and often produces small, red, pus-filled bumps. Left untreated, rosacea tends to worsen over time. Rosacea signs and symptoms may flare up for a period of weeks to months and then diminish before flaring up again. Rosacea can be mistaken for acne, an allergic reaction or other skin problems. While there's no cure for Rosacea, current treatments can only help to control and reduce the signs and symptoms of the condition.

Rosacea is typically observed in individuals after the age of thirty as redness on the cheeks, nose, chin or forehead that may come and go. In some cases, rosacea may also occur on the neck, chest, scalp or ears. Over time the redness tends to become ruddier and more persistent, and visible blood vessels may appear. Left untreated, bumps and pimples often develop and in severe cases the nose may grow swollen and bumpy from excess tissue. This is the condition, called rhinophyma (pronounced "rhi-no-FY-muh"), that gave the late comedian W. C. Fields his trademark bulbous nose. In many rosacea patients the eyes are also affected, feeling irritated and appearing watery or bloodshot.

Although rosacea can affect all segments of the population, individuals with fair skin who tend to flush or blush easily are believed to be at greatest risk. The disease is more frequently diagnosed in women, but more severe symptoms tend to be seen in men. Rosacea can vary substantially from one individual to another and in most cases some rather than all of the potential signs and symptoms appear. According to a consensus committee and review panel of 17 medical experts worldwide, rosacea always includes at least one of the following primary signs, and various secondary signs and symptoms may also develop.

As described in U.S. Pat. App. 61/953,920, primary signs of rosacea include: (1) Flushing: Many people with rosacea have a history of frequent blushing or flushing. This facial redness may come and go, and is often the earliest sign of the disorder. (2) Persistent Redness: Persistent facial redness is the most common individual sign of rosacea, and may resemble a blush or sunburn that does not go away. (3) Bumps and Pimples: Small red solid bumps or pus-filled pimples often develop. While these may resemble acne, blackheads are absent and burning or stinging may occur. (4) Visible Blood Vessels: In many people with rosacea, small blood vessels become visible on the skin. (6) Other Potential Signs and Symptoms include: Eye Irritation. In many people with rosacea, the eyes may be irritated and appear watery or bloodshot, a condition known as ocular rosacea. The eyelids also may become red and swollen, and styes are common. Severe cases can result in corneal damage and vision loss without medical help; Burning or Stinging: Burning or stinging sensations may often occur on the face. Itching or a feeling of tightness may also develop; Dry Appearance: The central facial skin may be rough, and thus appear to be very dry; Plaques: Raised red patches, known as plaques, may develop without changes in the surrounding skin; Skin Thickening: The skin may thicken and enlarge from excess tissue, most commonly on the nose. This condition, known as rhinophyma, affects more men than women; Swelling: Facial swelling, known as edema, may accompany other signs of rosacea or occur independently; Signs Beyond the Face: Rosacea signs and symptoms may also develop beyond the face, most commonly on the neck, chest, scalp or ears.

Various subtypes of rosacea include: Subtype 1 (erythematotelangiectatic rosacea), characterized by flushing and persistent redness, and may also include visible blood vessels; Subtype 2 (papulopustular rosacea), characterized by persistent redness with transient bumps and pimples; Subtype 3 (phymatous rosacea), characterized by skin thickening, often resulting in an enlargement of the nose from excess tissue; Subtype 4 (ocular rosacea), characterized by ocular manifestations such as dry eye, tearing and burning, swollen eyelids, recurrent styes and potential vision loss from corneal damage.

Many patients experience characteristics of more than one subtype at the same time, and those often may develop in succession. While rosacea may or may not evolve from one subtype to another, each individual sign or symptom may progress from mild to moderate to severe. Early diagnosis and treatment are recommended.

As described in U.S. Pat. App. No. 61/953,290 filed Mar. 14, 2014 to Spallitta, which is specifically incorporated by reference for the mechanistic explanations of rosacea, including literature related thereto, *Demodex* mites are a root cause of rosacea. Accordingly, provided herein are various treatments that specifically target this mechanism.

SUMMARY OF THE INVENTION

Provided herein are treatment methods that alleviate, abrogate, or otherwise reduce or stop any one or more of the above clinical symptoms by administering or applying an acetylcholinesterase inhibitor, including a carbamate, a naturally occurring acetylcholinesterase inhibitor and/or an ethyl carbamate.

Embodiments of the invention described herein involve treating skin afflictions by the topical or oral use of one or more than one acetylcholinesterase inhibitors including a carbamate, an ethyl carbamate, or a naturally occurring acetylcholinesterase inhibitor. By effectively reducing or eliminating the population of *Demodex* mites in affected skin areas and areas where *Demodex* mites may exist, this treatment achieves a more complete remission of clinical signs and symptoms of the skin afflictions than any previously described method. Embodiments of the invention are useful for treating skin afflictions including common acne, seborrheic dermatitis, perioral dermatitis, an acneform rash, transient acantholytic dermatosis, acne necrotica milliaris, psoriasis, steroid induced dermatitis, primary irritation dermatitis and rosacea.

An exemplary method embodiment comprises a step of orally-administering or topically-applying to an individual having the skin affliction an acetylcholinesterase inhibitor in a dosage sufficient to inactivate *demodex brevis* and/or *demodex folliculorum* mites from hair follicles and/or skin of the individual, resulting in amelioration or cessation of the manifestations of allergic and/or vasomotor responses to the mites that cause symptoms and signs of the skin affliction in the individual. Optionally, the skin affliction affects facial skin or eyelids, or both. In an embodiment, the acetylcholinesterase inhibitor is not an organophosphate, including any of the organophosphates described in WO 2015/017328.

In an exemplary embodiment, the acetylcholinesterase inhibitor is topically applied. In an embodiment, for example, the topically-applied acetylcholinesterase inhibitor is formulated in a carrier lotion, cream, soap, wash, shampoo or gel. Optionally, a concentration of the acetylcholinesterase inhibitor in the topically-applied lotion, cream, soap, wash, shampoo or gel is about 0.001 to 5 percent by weight or about 0.01 to 1 percent by weight. In an exemplary embodiment, a concentration of the acetylcholinesterase inhibitor in the topically-applied lotion, cream, soap, wash, shampoo or gel is a lowest concentration effective for killing the *demodex* mites. In one embodiment, a dosage of acetylcholinesterase inhibitor in the topically-applied lotion, cream, soap, wash, shampoo or gel is less than about 150 mg/kg of body mass or between about 0.01 mg per kg of body mass and 50 mg/kg of body mass. In an exemplary embodiment, a dosage of acetylcholinesterase inhibitor in the topically-applied lotion, cream, soap, wash, shampoo or gel is a lowest dose effective for killing the *demodex* mites. Optionally, the topically-applied acetylcholinesterase inhibitor is encapsulated inside microliposomes before being formulated into the carrier lotion, cream, soap, wash, shampoo or gel.

In general, methods of the invention include those where the topically-applied acetylcholinesterase inhibitor is applied to skin areas affected by the skin affliction. In certain embodiments, however, the topically-applied acetylcholinesterase inhibitor is further applied to skin areas not affected by the skin affliction. For example, in one embodiment, the topically-applied acetylcholinesterase inhibitor is applied to skin areas of the body where *demodex brevis* and/or *demodex folliculorum* mites exist. In an exemplary embodiment, the topically-applied acetylcholinesterase inhibitor is applied to all skin areas.

Optionally, methods of the invention further comprise a step of applying the acetylcholinesterase inhibitor to the individual's clothing, linens or both clothing and linens. Such application is useful, for example, for preventing the individual's clothing or linens from being a source of *demodex* mites to reintroduce onto the individual's skin. Similarly, methods of the invention optionally further comprise a step of orally-administering or topically-applying the acetylcholinesterase inhibitor to others having contact with the individual in a dosage sufficient to kill and eliminate *demodex brevis* and/or *demodex folliculorum* mites from hair follicles and/or skin of the others. For example, in embodiments, the others comprise household members, children, spouses, partners, family members or domestic pets.

In an exemplary embodiment of the methods of the invention, the topically-applied acetylcholinesterase inhibitor is applied to the hair follicles and/or skin of the individual. In one embodiment, for example, the topically-applied acetylcholinesterase inhibitor penetrates an outer layer of the skin of the individual, thereby exposing the *demodex brevis* and/or *demodex folliculorum* mites present below the outer layer of the skin to the acetylcholinesterase inhibitor. In one embodiment, for example, the topically-applied acetylcholinesterase inhibitor penetrates to a subdermal region of the skin of the individual, thereby exposing the *demodex brevis* and/or *demodex folliculorum* mites present in the subdermal region of the skin to the acetylcholinesterase inhibitor. Certain formulations of the topical acetylcholinesterase inhibitor useful with the methods of the invention optionally comprise one or more compositions that increase a permeability of the skin, such as dimethyl sulfoxide (DMSO).

In an exemplary embodiment, the topically-applied acetylcholinesterase inhibitor is applied to affected skin areas at least once and not more than twice daily for a period of about two to six weeks. In one embodiment, the topically-applied acetylcholinesterase inhibitor is applied to the affected skin areas and/or to non-affected skin areas during a first application period, thereby filling and eliminating adult *demodex brevis* and/or *demodex folliculorum* mites from the hair follicles in the skin of the individual. In one embodiment, the topically-applied acetylcholinesterase inhibitor is further applied to the affected skin areas and/or to non-affected skin areas during a second application period, thereby filling and eliminating from the hair follicles and/or skin of the individual *demodex brevis* and/or *demodex folliculorum* mites that have matured from a larval form and/or an egg form present on and/or in the skin during the first application period. In one embodiment, the topically-applied acetylcholinesterase inhibitor is further applied to the affected skin areas and/or to non-affected skin areas during a third application period, thereby filling and eliminating from the hair follicles and or skin of the individual *demodex brevis* and/or *demodex folliculorum* mites that have matured from a larval form and/or an egg form present on and/or in the skin and/or the hair follicles during the first application period and/or the second application period.

Optionally, the first application period and the second application period are separated by at least five but no more than ten days. Optionally, the first application period and the second application period are separated by at least seven days. In an exemplary embodiment, the first application period and the second application period are separated by a time sufficient to allow the larva form to mature into an adult form and/or to allow the egg form to mature into the adult form.

Optionally, the second application period and the third application period are separated by at least five but no more than ten days. Optionally, the second application period and the third application period are separated by at least seven days. In an exemplary embodiment, the second application period and the third application period are separated by a time sufficient to allow the larva form to mature into an adult form and/or to allow the egg form to mature into the adult form.

In exemplary embodiments, the acetylcholinesterase inhibitor is orally-administered or topically-applied in a continued intermittent regime sufficient for prophylactic control of *demodex* mite population in the hair follicles and/or skin of the individual.

In another embodiment, the acetylcholinesterase inhibitor is orally-administered. In a specific embodiment, for example, the orally-administered acetylcholinesterase inhibitor is administered as an oral dose of the acetylcholinesterase inhibitor of about 150 mg per kg of body mass or less or between about 0.01 mg per kg of body mass and 50 mg per kg of body mass. In an exemplary embodiment, the orally-administered acetylcholinesterase inhibitor is administered as an oral dose of the acetylcholinesterase inhibitor of a lowest dose effective for killing the *demodex* mites. In certain embodiments, the orally-administered acetylcholinesterase inhibitor is formulated as a prodrug or pharmaceutically acceptable salt.

Optionally, the orally-administered acetylcholinesterase inhibitor is administered as a daily dose of 10 mg per kg of body mass. Optionally, the orally-administered acetylcholinesterase inhibitor is administered as a daily dose of 7.5 mg per kg of body mass. Optionally, the orally-administered acetylcholinesterase inhibitor is administered as a three times per day dose of 5 mg per kg of body mass. Optionally, the orally-administered acetylcholinesterase inhibitor is repeated about two to four times with spacing of three to seven days between them.

In various embodiments, the elimination of the *demodex brevis* and/or *demodex folliculorum* mites from hair follicles and/or skin of the individual results in a reduction in population of one or more bacteria in the hair follicles and/or skin of the individual. For example, in some embodiments, the allergic and/or vasomotor responses to the mites result from a presence of one or more bacteria associated with the mites in the hair follicles and/or skin of the individual. In specific embodiments, the one or more bacteria comprise one or more bacteria from the genus *staphylococcus* or from the genus *bacillus*. For example, in one embodiment, the one or more bacteria comprise *bacillus oleronius* bacteria. In one embodiment, for example, the one or more bacteria comprise *Staphylococcus epidermidis* bacteria. Optionally, the one or more bacteria are present in a digestive system of the *demodex brevis* and/or *demodex folliculorum* mites.

Another exemplary method for treating a skin affliction comprises a step of topically-applying to an individual having the skin affliction an active ingredient in a dosage sufficient to fill and eliminate *demodex brevis* and/or *demodex folliculorum* mites from hair follicles and/or skin of the individual, resulting in cessation of the manifestations of allergic and/or vasomotor responses to the mites that cause symptoms and signs of the skin affliction in the individual, wherein the topically-applied active ingredient is applied to skin areas affected by the skin affliction and to skin areas not affected by the skin affliction. In a specific embodiment, the topically-applied active ingredient is applied to all skin of the individual, thereby filling and eliminating the *demodex brevis* and/or *demodex folliculorum* mites from all skin of the individual. Again, methods of the invention are useful, for example, for treating skin conditions including common acne, seborrheic dermatitis, perioral dermatitis, an acneform rash, transient acantholytic dermatosis, acne necrotica milliaris, psoriasis, steroid induced dermatitis, primary irritation dermatitis or rosacea. In an exemplary embodiment, the skin condition is caused by, exacerbated by or otherwise comorbid with an infestation of the skin and/or hair follicles by *demodex* mites.

In an aspect, the acetylcholinesterase inhibitor is a reversible inhibitor. Compounds that are reversible competitive or noncompetitive inhibitors of cholinesterase include those having therapeutic uses, including: Carbamates, Physostigmin, Neostigmine, Pyridostigmine, Ambenonium, Demecarium, Rivastigmine, Phenanthrene derivatives, Galantamine, Caffeine—noncompetitive (also an Adenosine receptor antagonist)[13][14], Piperidines, Donepezil, Tacrine, also known as tetrahydroaminoacridine (THA'), Edrophonium, Huperzine A[15][16], Ladostigil, Ungeremine[17], and Lactucopicrin.

In an aspect, the acetylcholinesterase inhibitor is a quasi-reversible inhibitor. Compounds which function as quasi-irreversible inhibitors of cholinesterase tend to have use as pesticides. These include organophosphates and carbamates. Examples of organophosphates include: Echothiophate, Diisopropyl fluorophosphates, Cadusafos, Chlorpyrifos, Dichlorvos, Dimethoate, Metrifonate (irreversible), Malathion and Parathion. Examples of carbamates include: Aldicarb; Bendiocarb; Bufencarb; Carbaryl; Carbendazim; Carbetamide; Carbofuran; Carbosulfan; Chlorbufam; Chloropropham; Ethiofencarb; Formetanate; Methiocarb; Methomyl; Oxamyl; Phenmedipham; Pinmicarb; Pirimicarb; Propamocarb; Propham; Propoxur; Huperzine A; Galantamine; Onchidal; Coumarins.

In another embodiment, the acetylcholinesterase inhibitor corresponds to a compound currently used in medicine, including those having an established safety profile in humans. Examples include: Aricept; Aricept ODT; Cognex; donepezil; Exelon; galantamine; Namzaric; Razadyne; rivastigmine; tacrine; phospholine; neostigmine; parathion; malathion; dyflos; physostigmine; endrophonium; pyridostigmine; ecothiapate.

Statements Regarding Chemical Compounds and Nomenclature

In an embodiment, a composition or compound used with the methods of the invention is isolated or purified. In an embodiment, an isolated or purified compound is at least partially isolated or purified as would be understood in the art. In an embodiment, the composition or compound of the invention has a chemical purity of 95%, optionally for some applications 99%, optionally for some applications 99.9%, optionally for some applications 99.99%, and optionally for some applications 99.999% pure.

Many of the compounds used in the methods of the invention contain one or more ionizable groups. Ionizable groups include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The term "carbamate" generally refers to an organic compound derived from carbamic acid (NH$_2$COOH), such as NR$_2$R$_3$COOR$_1$:

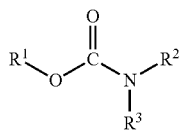

In an aspect, each of the groups R1-R3 are independently selected to correspond to any of the R groups of the chemicals listed herein. In an aspect, any of R1-R3 are hydrogen.

Examples of carbamates for use with the methods described herein include, but are not limited to, neostigmine, rivastigmine, meprobamate, carisoprodol, felbamate, tybamate. Preferred carabamates are those that have been demonstrated to have miticidal or insecticidal capabilities and that can be provided to a mite on the skin at a level sufficient to inactivate or kill the mite without permanently adversely affecting the host patient. The carbamate may be a naturally occurring compound, such as a purified and isolated naturally occurring compound. Alternatively, the carbamate may be a synthetically produced carbamate, as known in the art. Any of the compounds provided herein may be provided in the form of a derivative, prodrug, or a pharmaceutically acceptable salt thereof.

In an aspect, the carbamate is selected from the group consisting of: aldicarb, bendiocarb, bufencarb, carbaryl, carbendazim, carbetamide, carbofuran, carbosulfan, chlorbufam, chloropropham, ethiofencarb, formetanate, methiocarb, methomyl, oxamyl, phenmedipham, pinmicarb, pirimicarb, propamocarb, propham, propoxur, butocarboxim, carbanolate, promacyl, thiocarboxime, thiofanox, benomyl, and metolcarb or a derivative, prodrug or pharmaceutically acceptable salt thereof.

In an aspect, the carbamate is an ethyl carbamate of the form R$_1$=ethyl. R$_2$ and R$_3$ are optionally independently selected as hydrogen.

The compounds used in the methods of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, -32-cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, di hydrogen phosphoric, phthalic, polygalacturonic, propionic, salicylic, stearic, succinic, sulfamic, sulfanlic, sulfonic, sulfuric, tannic, tartaric, teoclic, toluenesulfonic, and the like. Pharmaceutically acceptable salts may be derived from amino acids, including but not limited to cysteine. Other pharmaceutically acceptable salts may be found, for example, in Stahl et al., Handbook of Pharmaceutical Salts: Properties, Selection, and Use, Wiley-VCH; Verlag Helvetica Chimica Acta, Zürich, 2002. (ISBN 3-906390-26-8). Pharmaceutically-acceptable cations include among others, alkali metal cations (e.g., Li$^+$, Na$^+$, K$^+$), alkaline earth metal cations (e.g., Ca$^{2+}$, Mg$^{2+}$), non-toxic heavy metal cations and ammonium (NH$_4^+$) and substituted ammonium (N(R')$_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl$^-$, Br$^-$), sulfate, acetates (e.g., acetate, trifluoroacetate), ascorbates, aspartates, benzoates, citrates, and lactate.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Inactivate" is used broadly herein to refer to the functional ability to decrease the impact of *demodex brevis* and/or *demodex folliculorum* mites. For example, the inactivation may be by death of the mite. Alternatively, the inactivation may refer to the inability of the mite to reproduce, so that the mite die off occurs as the mites age and die without reproduction. So long as the treatment leads to an adverse effect on the *demodex brevis* and/or *demodex folliculorum* mites that corresponds to improved clinical outcome, such as symptom improvement, the treatment is considered herein to inactivate *demodex brevis* and/or *demodex folliculorum* mites.

*D. folliculorum* and *D. brevis* mites may play a role in the rosacea condition. An increased *demodex* population has been observed in rosacea patients. For most people, *demodex* mites live harmlessly in the skin as a result of either down-regulating host immunity or simply dodging host immune defenses. There is vociferous debate within the dermatology community as to whether or not they are the causative agents of such skin diseases as rosacea and blepharitis (inflammation of the eyelids) a common issue seen in rosacea patients.

Human beings are the one and only host of this ubiquitous mite [1]. In fact, these two mites are considered to be the most common ectoparasite of humans [6]. Women tend to have a higher rate of *demodex* infections [5]. The rate of infestation also seems to be correlated with age, with 84% of people at age 60 harboring mites and increasing to 100% in those 70 years and older [7]. Whether those that are immunocompromised are more susceptible to higher infestation rates is unknown, though some studies indicate that AIDs and leukemia patients may be more prone to greater than average numbers [5].

The mites are most commonly found in the scalp, face and upper chest area, with *D. folliculorum* exhibiting a predilection for the hair follicles and *D. brevis* for the sebaceous ducts and meibomian glands at the rim of the eyelids (the sebaceous ducts transfer the waxy sebum that lubricates the skin and hair from the sebum glands; the meibonmian glands are a special type of such gland) [4][5]. *D. folliculorum* are a communal bunch, tending to congregate in the follicle area of the hair or eyelashes with their posterior ends protruding from the follicular pores. *D. brevis*, on the other hand, tend to be more solitary and will occupy the sebaceous glands singly [6]. Both species are tiny, less than 0.4 mm, with elongated, clear bodies and four pairs of stout legs. *D. brevis* is usually a tad shorter, ~0.1 mm, than *D. folliculorum*. They both have ridged scales along their cephalothorax and sharp, piercing teeth [6].

Short-lived creatures, a mite's life cycle from egg to larva to adult lasts from 14-18 days. Adults emerge from the follicles and ducts to reproduce at the surface of the skin where females will then deposit eggs in the sebaceous glands. Larva will mature via two nymphal stages in the glands until entering the follicles and ducts as adults to begin the cycle anew [6]. It is hypothesized that both species of mites feed upon sebum as a primary food source but may also munch on follicular and glandular epithelia. They are thought to be obligate ectoparasites, incapable of living outside their human host.

Some studies have discovered a greater than average mite density, greater than five mites per $cm^2$, do seem to play a role in these two diseases for patients [6]. Researchers have suggested that blockage of the hair follicles and sebaceous ducts by mites may result in epithelial hyperplasia, elicit a phagocytic, granulomatous reaction or bring about an inflammatory response due to their waste products [5]. The fact that treatment with certain antibiotics can reduce the severity of rosacea strongly suggests a microbial component to mite-related diseases. Indeed, in 2007, researchers isolated from *D. folliculorum* a bacterium *Bacillus oleronium* that provoked inflammatory responses in 73% of rosacea patients but only 29% of controls [21]. These results suggest that patients with rosacea were sensitized to the bacteria and may be immunologically sensitive to the mites, bacteria or both [21].

Two antigenic proteins found on the bacterium's cell surface in particular appeared to be responsible for the inflammatory response by stimulating peripheral blood mononuclear cell proliferation; one 83 kDa protein showed similarity with heat-shock proteins while the other 62 kDa protein shared amino acid sequence homology with a protease enzyme found to be involved signal transduction as well as carbohydrate metabolism [21]. Stronger proof of the pathogenic role of *B. oleronius* in rosacea may also be found in the sensitivity of the bacterium to many antibiotics proven to be effective in the treatment of rosacea, specifically tetracycline, doxycycline and minocycline [21].

In an exemplary embodiment, an acetylcholinesterase inhibitor is administered topically to a patient with an active skin condition in which the underlying cause is a *demodex* mite. Because the target organisms, *demodex brevis* and *demodex folliculorum*, are ectoparasites in the mite family, an effective treatment must be capable of eradicating the entire lifecycle of such a microscopic insect, including egg, larval, and adult stages. For this reason, this embodiment treats such patients with several doses. Such spacing allows time for *demodex* eggs to hatch into immature mites that are killed before they can mature into egg-producing adults. After the acetylcholinesterase inhibitor carries out its miticidal activity on skin *demodex brevis* and *demodex folliculorum* organisms, inflammatory responses to them begin to diminish but remnants of the dead mites still elicit some flushing and lesion formation until the cleanup processes of the body remove them, a process requiring six to eight weeks. During this initial phase of acetylcholinesterase inhibitor administration, conventional antirosacea medications such as oral tetracycline and topical metronidazole can optionally be employed to suppress early flareups and to give early clinical response. No such medications are needed to treat manifestations of rosacea after six to eight weeks have elapsed. After prolonged intervals of freedom from rosacea symptoms, should classic signs begin to reappear, treatment can be repeated. Such retreatments are optionally unnecessary more than one or two times per year. The acetylcholinesterase inhibitor is formulated into a cosmetically-acceptable topical lotion, cream, shampoo, or gel and applied especially to skin affected by rosacea and any area possibly inhabited by *demodex brevis* and *demodex folliculorum*. Because of the well-known barrier effect the skin presents to the penetration of topical medications, such a route of treatment with acetylcholinesterase inhibitor is anticipated to require once or twice daily applications for as long as six weeks to achieve sufficient follicle penetration and effective miticidal activity. A topical formulation that could achieve this effect would contain about 5% or less of the acetylcholinesterase inhibitor. The lesser the percentage of the acetylcholinesterase inhibitor that can be used while still receiving the miticidal effect and successfully treating the skin condition is ideal for limiting any possible side effects of the chemical. Further, full body treatment is optionally useful for preventing reintroduction of the mites onto skin, such as facial skin, from other body locations.

Medical Use of Carbamates:

Urethane (ethyl carbamate) was once produced commercially in the United States as an antineoplastic agent and for other medicinal purposes. It was found to be toxic and largely ineffective. It is occasionally used as a veterinary medicine.

In addition, some carbamates are used in human pharmacotherapy, for example, the cholinesterase inhibitors neostigmine and rivastigmine, whose chemical structure is based on the natural alkaloid physostigmine. Other examples are meprobamate and its derivatives like carisoprodol, felbamate, and tybamate, a class of anxiolytic and muscle relaxant drugs widely used in the 60s before the rise of benzodiazepines, and still used nowadays in some cases.

The cholinesterase inhibitors neostigmine and rivastigmine may be efficacious if they have similar miticidal capabilities compared to many other carbamate compounds.

Drug class and mechanism: Rivastigmine is an oral medication used to treat patients with Alzheimer's disease. Rivastigmine is in a class of drugs called cholinesterase inhibitors that also includes tacrine (Cognex), donepezil (Aricept), and galantamine (Razadyne—formerly known as Reminyl).

Cholinesterase inhibitors inhibit (block) the action of acetylcholinesterase, the enzyme responsible for the destruction of acetylcholine. Acetylcholine is one of several neurotransmitters in the brain, chemicals that nerve cells use to communicate with one another. Reduced levels of acetylcholine in the brain are believed to be responsible for some of the symptoms of Alzheimer's disease.

Rosacea flares explained through the human consumption of the naturally occurring insecticide ethyl carbamate which is contained in foods and beverages produced using fermentation and from trace insecticidal residues from agricultural practices and naturally occurring acetylcholinesterase inhibitors used in fragrances and cosmetics.

Ethyl Carbamates are a group of chemical compounds having insecticidal capabilities, especially as acaricides and miticides. Rosacea is a disease caused by the proliferation of *bacillus oleronius*. *Bacillus oleronius* is a Gram-negative bacterium belonging to the genus *Bacillus*. It is also found in the human skin parasitic mite *Demodex folliculorum*, and is related to the development of a type of acne rosacea.[1]

Triggers that cause episodes of flushing and blushing play a part in the development of rosacea. Exposure to temperature extremes can cause the face to become flushed as well as strenuous exercise, heat from sunlight, severe sunburn, stress, anxiety, cold wind, and moving to a warm or hot environment from a cold one such as heated shops and offices during the winter. There are also some food and drinks that can trigger flushing, including alcohol, food and beverages containing caffeine (especially, hot tea and coffee), foods high in histamines and spicy food. Foods high in histamine (red wine, aged cheeses, yogurt, beer, cured pork products such as bacon, etc.) can even cause persistent facial flushing in those individuals without rosacea due to a separate condition, histamine intolerance.

Certain medications and topical irritants can quickly trigger rosacea. Some acne and wrinkle treatments that have been reported to cause rosacea include microdermabrasion and chemical peels, as well as high dosages of isotretinoin, benzoyl peroxide, and tretinoin. Steroid induced rosacea is the term given to rosacea caused by the use of topical or nasal steroids. These steroids are often prescribed for seborrheic dermatitis. Dosage should be slowly decreased and not immediately stopped to avoid a flare up.

A survey by the National Rosacea Society of 1,066 rosacea patients showed which factors affect the most people [2], as summarized in the TABLE 1:

| Foods |
| --- |
| Liver |
| Yogurt |
| Sour cream |
| Cheese (except cottage cheese) |
| Chocolate |
| Vanilla |
| Soy sauce |
| Yeast extract (bread is OK) |
| Vinegar |
| Eggplant |
| Avocados |
| Spinach |
| Broad-leaf beans and pods, including lima, navy or pea |
| Citrus fruits, tomatoes, bananas, red plums, raisins or figs |
| Spicy and thermally hot foods |
| Foods high in histamine |

| Beverages |
| --- |
| Alcohol, especially red wine, beer, bourbon, gin, vodka or champagne |
| Hot drinks, including hot cider, hot chocolate, coffee or tea |

| Emotional influences |
| --- |
| Stress |
| Anxiety |

| Skin care products |
| --- |
| Some cosmetics and hair sprays, especially those containing alcohol, witch hazel or fragrances |
| Hydro-alcoholic or acetone substances |
| Any substance that causes redness or stinging |

| Temperature-related |
| --- |
| Saunas |
| Hot baths |
| Simple overheating |
| Excessively warm environments |

| Weather |
| --- |
| Sun |
| Strong winds |
| Cold |
| Humidity |

| Drugs |
| --- |
| Vasodilators |
| Topical steroids |

| Medical conditions |
| --- |
| Frequent flushing |
| Menopause |
| Chronic cough |
| Caffeine withdrawal syndrome |

| Physical exertion |
| --- |
| Exercise |
| "Lift and load" jobs |

| | |
| --- | --- |
| Sun exposure | 81% |
| Emotional stress | 79% |
| Hot weather | 75% |
| Wind | 57% |
| Heavy exercise | 56% |
| Alcohol consumption | 52% |
| Hot baths | 51% |
| Cold weather | 46% |
| Spicy foods | 45% |
| Humidity | 44% |
| Indoor heat | 41% |
| Certain skin-care products | 41% |
| Heated beverages | 36% |
| Certain cosmetics | 27% |
| Medications | 15% |
| Medical conditions | 15% |
| Certain fruits | 13% |
| Marinated meats | 10% |
| Certain vegetables | 9% |
| Dairy products | 8% |
| Other factors | 24% |

It should be noted however that there exists significant disagreement amongst sufferers and clinicians as to the validity of these aggravators/triggers being categorized as causes of rosacea. The claim of rosacea being caused (as opposed to aggravated) by the above list has not been established by epidemiological scientific study.[22] Many sufferers report that elimination of triggers has little or no eventual impact on the actual progression of the disease. The above list should in no way be taken as an explanation of rosacea causes, as the spectrum disease is more complex than simply a direct or sole result of habits and diet.

It has been long hypothesized that food with high histamines are responsible for rosacea flares. However histamine intolerance should be seen as a separate condition from rosacea. Antihistamines have no effect on rosacea patient flares. If flushing occurs with red wine consumption, then complete avoidance is the only thing that helps. There is absolutely no evidence at all that antihistamines are of any benefit in treating rosacea. If histamines were responsible for rosacea flares than logically antihistamines should have some effect on the flares. It should also be noted that many foods containing high histamine levels like eggs and mushrooms have never been cited as inducing rosacea flushing.

The mechanistic explanation provided herein is that all rosacea triggers can be explained by either temperature changes or trace insecticide consumption affecting *demodex* mites especially ethyl carbamates. Many foods listed as inducing rosacea flares have naturally occurring pesticides or trace insecticidal residues from agricultural manufacturing practices.

Ethyl carbamate has been found to occur in food made by a fermentation process, including beer, wine, whiskey, brandy, bread, soy sauce, and yogurt.[23] Carbamates are very effective miticides due to their ability to inhibit acetylcholinesterase. Mites are extremely sensitive to acetylcholinesterase inhibitors. Accordingly, trace amounts of ethyl carbamates may cause *demodex* mites in rosacea patient's epidermis to die or be agitated and excrete the *bacillus* O. bacteria into the rosacea patient's epidermis. This triggers the immediate immune response we observe as rosacea flushing. A list of foods associated with rosaces flares and their connection to insecticides is provided below with an explanation of the connection to temperature or trace insecticidal oral consumption.

Coffee or caffeine: The National Rosacea Society lists coffee or caffeine as causing rosacea flares as the number one myth about rosacea. Drake, L.[27] Although coffee and caffeine are widely reported to cause rosacea flares conventional thought among dermatologists has been that the flares are caused by the heat of the beverage and not the caffeine. [28] The mechanistic explanation for coffee causing rosacea flares provided herein is that it is multifactorial with both the heat and the caffeine causing the flare. Temperatures above 37° C. are harmful to *demodex* mites.[25] Caffeine is an acetylcholinesterase inhibitor.[29] Mites have a hypersensitivity to acetylcholinesterase inhibitors, in fact many miticides are acetylcholinesterase inhibitors.[30]

Liver: Liver has been found to have higher insecticidal concentrations than other cuts of beef. Both carbamates and organophosphates are feed to cattle and are very commonly applied to the backs of cattle. Accumulation of these compounds in the liver is a very real possibility.

Yogurt: Yogurt contains naturally occurring trace carbamates from the process of fermentation Sour cream: Sour Cream contains naturally occurring trace carbamates from the process of fermentation Cheese (except cottage cheese): Cheese contains naturally occurring trace carbamates from the process of fermentation Chocolate: Chocolate has been reported to contain trace amounts of Lindane and other organochlorine pesticides. [24] These trace amounts of insecticides are affecting the mite possibly even killing them. Lindane is a commonly used scabicide so we know it's effective in killing mites.

Vanilla: Vanilla is commonly used as a natural insecticide and may be adversely affecting *demodex* mites in people who consume it.

Soy sauce: Soy Sauce contains naturally occurring trace carbamates from the process of fermentation.

Yeast extract (bread is OK): Yeast extract contains naturally occurring trace carbamates from the process of fermentation.

Vinegar: Vinegar contains naturally occurring trace carbamates from the process of fermentation. Vinegar is commonly used as a natural insecticide.

Eggplant; Avocados; Spinach; Broad-leaf beans and pods, including lima, navy or pea; Citrus fruits, tomatoes, bananas, red plums, raisins or figs: All of these plants have been known to contain trace amounts of insecticide and pesticides. These plants are all susceptible to mite infestation or other similar pests for which miticides are used to control during agricultural production.

Spicy and thermally hot foods: Animal and human studies have demonstrated that the oral intake of capsaicin may increase the production of heat by the body for a short time. Temperatures above 37 C are harmful to *demodex*.[25] Any increase in human body temperature will result in agitating the mites. Most spicy foods contain capsaicin. Capsaicin is well known as being a natural pesticide. The first pesticide product using solely capsaicin as the active ingredient was registered with the U.S. Department of Agriculture in 1962. [26] It could be hypothesized that ingestion of capsaicin a naturally occurring miticide is killing or adversely affecting the mite.

Foods high in histamine: Histamine rich foods cause redness in people who have histamine intolerance which is a separate condition than rosacea but can cause facial redness or flushing. Food manufactured using the process of fermentation tends to be high in histamines but also in carbamates. However foods with high histamines not associated with the process of fermentation do not reportedly cause rosacea flares.

Beverages

Alcohol, especially red wine, beer, bourbon, gin, vodka or champagne: Alcohol but especially red wine contains naturally occurring trace carbamates from the process of fermentation. Also alcohol itself is a miticide. Elevated blood alcohol levels will likely agitate or kill the mites. Red wine one of the most well known and well documented causes of rosacea flares tends to have the highest concentrations of carbamates of any alcoholic beverages.

Hot drinks, including hot cider, hot chocolate, coffee or tea: Drinking hot drinks will slightly increase facial temperature agitating or killing the mites.[25]

Skin care products: Some cosmetics and hair sprays, especially those containing alcohol, witch hazel or fragrances; Hydro-alcoholic or acetone substances; Any substance that causes redness or stinging.

Cosmetics commonly contain carbamates and alcohol commonly used in skin care products is a miticide. Witch hazel listed above is used as a natural insecticide or pest repellant. Also many fragrances contain alcohol or trace amounts of compounds like *Boswellia sacra* resin which is used to produce frankincense, also called olibanum, which is an aromatic resin obtained from trees of the genus *Boswellia*, particularly *Boswellia sacra*. Frankincense is commonly used in fragrances and cosmetics. *Boswellia sacra* resin is a naturally occurring acetylcholinesterase inhibitor so it should be capable of being used to kill *demodex* and possibly treat rosacea.

Coumarin is another naturally occurring acetylcholinesterase inhibitor it is a fragrant organic chemical compound in the benzopyrone chemical class, which is a colorless crystalline substance in its standard state. It is a natural substance found in many plants. The name comes from a French term for the tonka bean, coumarou, one of the sources from which coumarin was first isolated as a natural product in 1820. It has a sweet odor, readily recognised as the scent of new-mown hay, and has been used in perfumes since 1882. There are five naturally occurring acetylcholinesterase inhibitors that may also kill *demodex* and might be affective for treating rosacea. They are listed below.

Other naturally occurring acetylcholinesterase inhibitors below could also be targeted in proper formulations to kill *demodex* mites and treat rosacea. The causation between flushing and these naturally occurring compounds used in fragrances and cosmetics that cause flushing may also be used to kill the *demodex* mite which is proliferating *bacillus* o. bacteria in the human epidermis causing rosacea patients to have an immune response to the bacteria.

Naturally occurring carbamates are acetycholinesterase inhibitors and have miticidal capabilities. Examples of natural compounds that exhibit the ability to inhibit acetylcholinesterase: Huperzine A; Glantamine; Onchidal; Coumarins; *Celastrus paniculatus; Boswellia*.

Patient 1. A 30 year old Caucasian male, weighing about 83 kg, exhibiting clinical evidence of rosacea for 3 years and had been treated with limited success with oral tetracycline and topical metronidazole and topical cortisones. Facial skin exhibits midfacial erythema and flushing with papule and pustule formation. In addition, eyelids exhibit chronic blepharitis. The skin also exhibited scaling and flaking.

The acetylcholinesterase inhibitor dichlorvos, 1% solution by weight with a volumetric application of about 1.2 mg/kg of body weight is administered to the patient. Patient found remission of the rosacea skin affliction after the treatment with a 1% dichlorvos solution. See, e.g., PCT Pub. No. WO 2015/017328, which is specifically incorporated by reference to the extent not inconsistent herewith. *Demodex* have extreme sensitivity to acetylcholinesterase inhibitors like dichlorvos. The author can see the use of carbamates as acetycholinesterase inhibitors in the treatment of rosacea orally or topically. Specifically neostigmine and rivastigmine the two acetycholinesterase inhibitors that are currently used to treat Alzheimer's Disease. Other compounds currently being evaluated include but are not limited to the following carbamates: Aldicarb; Bendiocarb; Bufencarb; Carbaryl; Carbendazim; Carbetamide; Carbofuran; Carbosulfan; Chlorbufam; Chloropropham; Ethiofencarb; Formetanate; Methiocarb; Methomyl; Oxamyl; Phenmedipham; Pinmicarb; Pirimicarb; Propamocarb; Propham; Propoxur; Butocarboxim; Carbanolate; Promacyl; Thiocarboxime; Thiofanox; Benomyl; Metolcarb.

REFERENCES

[1] Kligman A M & Christensen M S. (2011) *Demodex folliculorum*: Requirements for Understanding Its Role in Human Skin Disease. *Journal of Investigative Dermatology*. 131: 8-10

[2] Despommier, D, Gwadz R W, Hotez P J and Knirsch C A. Parasitic Diseases. 5th ed. New York: Apple Trees Production, LLC. 2006

[3] Hsu C K, Hsu M M, Lee J Y. (2009) Demodicosis: a clinicopathological study. *J Am Acad Dermatol*. 60(3): 453-62

[4] Lacey N, Kavanagh K, Tseng S C. (2009) Under the lash: *Demodex* mites in human diseases. *Biochem (Lond)*. 31(4): 2-6

[5] Liva J, Sheha H, & Tsenga S C G. (2010) Pathogenic role of *Demodex* mites in blepharitis. *Curr Opin Allergy Clin Immunol*. 10(5): 505-510.

[6] Thomson, W. T. 1976. Agricultural chemicals—book 1: insecticides, acaricides, and ovicides. Revised ed. Thomson Publ., Indianapolis, Ind. 232 pp.

[7] The Pesticide Manual: A World Compendium, 7th ed. 1983. C. R. Worthing, ed. The British Crop Protection Council, Croydon, England. 695 pp.

[8] U. S. Department of Health and Human Services, National Institute for Occupational Safety and Health. 1981. Occupational health guidelines for chemical hazards. F. W. Mackinson, R. S. Stricoff, L. J. Partridge, Jr., and A. D. Little, Inc., eds. DHHS (NIOSH) Publ. No. 81-123. Washington, D.C.

[9]. American Conference of Governmental Industrial Hygienists. 1984. TLVs: threshold limit values for chemical substances and physical agents in the work environment and biological exposure indices with intended changes for 1984-85. Cincinnati, Ohio 116 pp.

[10] Farm Chemicals Handbook, 70th ed. 1984. R. T. Meister, G. L. Berg, C. Sine, S. Meister, and J. Poplyk, eds. Meister Publishing Co., Willoughby, Ohio.

[11] *Demodex* mites: Facts and controversies. Elston D M. Department of Dermatology, Geisinger Medical Center, 100 N Academy Ave, Danville, Danville, Pa. 17822-5206, USA. Clin Dermatol. 2010 September-October; 28(5): 502-504.

[12] Mite-related bacterial antigens stimulate inflammatory cells in rosacea. Lacey N, Delaney S, Kavanagh K, Powell F C. Br J Dermatol. 2007 September; 157(3):474-81. Epub 2007 Jun. 26

[13] *The potential role of Demodex folliculorum mites and bacteria in the induction of rosacea*. Stanisław Jarmuda, Niamh O'Reilly, Ryszard Żaba, Oliwia Jakubowicz, Andrzej Szkaradkiewicz and Kevin Kavanagh. Journal of Medical Microbiology, 2012 DOI: 10.1099/jmm.0.048090-0 Article at PubMed

[14] *Positive correlation between serum immuno-reactivity to Demodex-associated Bacillus proteins and Erythema-totelangiectic$^{Rosacea}$*. O'Reilly N, Menezes N, Kavanagh K. Br J Dermatol. 2012 Jun. 18. doi: 10.1111/j.1365-2133.2012.11114.x.

[15] Rosacea Review, Fall 2010, NRS-Funded Studies Advance Knowledge of Rosacea's Causes

[16] Rosaceam Like Demodicidosis, SAMUEL AYRES, JR., M.D., Los Angeles Calif. Medicine, June 1963

[17] Something to Blush About, Medical Breakthoughs, Ivanhoe Newswire, Dec. 11, 2007, citing British Journal of Dermatology, 2007; 157:474-481

[18] Rosacea Diagnosis and Management, pages 69, 70 by Frank C. Powell, Informa Healthcare, 2008

[19] Empirical treatment is key to identifying rosacea, other dermatoses, Modern Medician, John Jesitus, Nov. 1, 2007

[20] "New Study Shows Role for Bacteria in Development of Rosacea Symptoms" (Press release). National Rosacea Society. 2004 May 3. Retrieved 2008 Sep. 27.

[21] Rosacea.org: The National Rosacea Society

[22] Lisa Faulkner: My unsightly rosacea—Celebrity gossip on Now Magazine

[23] U.S. Department of Health and Human Services. Hazardous Substances Databank (HSDB, online database). National Toxicology Information Program, National Library of Medicine, Bethesda, Md. 1993.

[24] Gordts, L., and van Haver, W. (1972). [Detection and determination of lindane and other organochlorine pesticides in chocolate]. Arch Belg Med Soc 30, 170-176.

[25] Ya E Zhao, Na Guo, Li Ping W U (January 2009) "The Effect of temperature on the viability of *Demodex folliculorum* and *Demodex brevis*.

[26] "R.E.D. Facts for Capsaicin". United States Environmental Protection Agency. Retrieved 2012-11-13.

[27] Drake, L. (2003, Apr. 1). Q&A: Coffee or Tea @ Localized Flare-ups. Retrieved Jun. 11, 2015. http://www.rosacea.org/rr/2003/spring/qa.php

[28] Wilkin J. Oral thermal-induced flushing in erythematelangiectatic rosacea. Journal of Investigative Dermatology.

[29] Pohanka M1, Dobes P. Caffeine inhibits acetylcholinesterase, but not butyrylcholinesterase. Int J Mol Sci. 2013 May 8; 14(5):9873-82. doi: 10.3390/ijms14059873. Military Health Sciences, University of Defense, Trebesska 1575, 50001 Hradec Kralove, Czech Republic.

[30] Čolović, M., Krstić, D., Lazarević-Pašti, T., Bondžić, A., & Vasić, V. (n.d.). Acetylcholinesterase Inhibitors: Pharmacology and Toxicology. Retrieved Jun. 11, 2015, from http://www.ncbi.nlm.nih.gov/pmc/articles/PMC3648782/

Supporting references for Ethyl Carbamates occurring in food and beverages associated with Rosacea flares.

NTP National Toxicology Program, NIEHS, National Institutes of Health, Eleventh Report on Carcinogens, Urethane, 2005. *Accessed* May 13, 2006

Segal, M Too Many Drinks Spiked with Urethane, US Food and Drug Administration, September 1988

Haddon W F, M I Mancini, M Mclaren, A Effio, L A Harden, R I Egre, & J L Bradford (1994). Cereal Chemistry 71 (2): 207-215.

Matsudo T, T Aoki, K Abe, N Fukuta, T Higuchi, M Sasaki & K Uchida (1993). "Determination of ethyl carbamate in soy sauce and its possible precursor". J Agric Food Chem 41 (3): 352-356. doi:10.1021/jf00027a003.

American Journal of Enology and Viticulture 57 (2): 113-124. 2006.

Butzke, C E & L F Bisson, Ethyl Carbamate Preventative Action Manual, Depart. of Viticulture & Enology, U. of CA, Davis, Calif., for US FDA, 1997 accessed May 13, 2006 www.ec.gc.ca/subsnouvelles-newsubs/default.asp?lang.En&n.AECC21AD-1

Zhao et al. "A met-analysis of association between acne vulgaris and *Demodex* infestation." J. Zhejiang Univ.—Sci B (Biomed & Biotechnol) 2012:13(3):192-202.

Example: Administration and Formulation

Salts and Prodrugs: The invention contemplates pharmaceutically active compounds either chemically synthesized or formed by in vivo biotransformation to compounds set forth herein.

Compounds of this invention and compounds useful in the methods of this invention include those of the compounds and formula(s) described herein and pharmaceutically-acceptable salts and esters of those compounds. In embodiments, salts include any salts derived from the acids and bases of the formulas herein which are acceptable for use in human or veterinary applications. In embodiments, the term ester refers to hydrolyzable esters of compounds of the names and formulas herein. In embodiments, salts and esters of the compounds of the formulas herein can include those which have the same or better therapeutic, diagnostic, or pharmaceutical (human or veterinary) general properties as the compounds of the formulas herein. In an embodiment, a composition of the invention is a compound or salt or ester thereof suitable for pharmaceutical formulations.

Compounds of the invention and used in the methods of the invention can have prodrug forms. Prodrugs of the compounds of the invention are useful in embodiments including compositions and methods. Any compound that will be converted in vivo to provide a biologically, pharmaceutically, diagnostically, or therapeutically active form of a compound of the invention is a prodrug. Various examples and forms of prodrugs are well known in the art. Examples of prodrugs are found, inter alia, in: Design of Prodrugs, edited by H. Bundgaard, (Elsevier, 1985); Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191 (1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug, can represent prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of a compound described herein, for example, by hydrolysis in blood or by other cell, tissue, organ, or system processes. Further discussion is provided in: T. Higuchi and V. Stella, Pro-drugs as Novel Delivery Systems, V. 14 of the A.C.S. Symposium Series; and in Edward B. Roche, ed., Bioreversible Carriers in Drug Design, American Pharmaceutical Association and Pergamon Press (1987).

Active ingredients of the invention can be formulated with pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include, among others, halides (e.g., $F^-$, $Cl^-$, $Br^-$, $At^-$), sulfate, acetates (e.g., acetate, trifluoroacetate), ascorbates, aspartates, benzoates, citrates, and lactate.

Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalacturonic, propionic, salicylic, stearic, succinic, sulfamic, sulfanlic, sulfonic, sulfuric, tannic, tartaric, teoclic, toluenesulfonic, and the like. Pharmaceutically acceptable salts can be derived from amino acids, including, but not limited to, cysteine. Other pharmaceutically acceptable salts can be found, for example, in Stahl et al., Handbook of Pharmaceutical Salts: Properties, Selection, and Use, Wiley-VCH, Verlag Helvetica Chimica Acta, Zürich, 2002. (ISBN 3-906390-26-8).

Efficacy: Typically, a compound of the invention, or pharmaceutically acceptable salt thereof, is administered to a subject in a diagnostically or therapeutically effective amount. One skilled in the art generally can determine an appropriate dosage.

Compositions for oral administration can be, for example, prepared in a manner such that a single dose in one or more oral preparations contains at least about 20 mg of the present compound per square meter of subject body surface area, or at least about 50, 100, 150, 200, 300, 400, or 500 mg of the present compound per square meter of subject body surface area (the average body surface area for a human is, for example, 1.8 square meters). In particular, a single dose of a composition for oral administration can contain from about 20 to about 600 mg, and in certain aspects from about 20 to about 400 mg, in another aspect from about 20 to about 300 mg, and in yet another aspect from about 20 to about 200 mg of the present compound per square meter of subject body surface area. Compositions for parenteral administration can be prepared in a manner such that a single dose contains at least about 20 mg of the present compound per square meter of subject body surface area, or at least about 40, 50, 100, 150, 200, 300, 400, or 500 mg of the present compound per square meter of subject body surface area. In particular, a single dose in one or more parenteral preparations contains from about 20 to about 500 mg, and in certain aspects from about 20 to about 400 mg, and in another aspect from about 20 to about 450 mg, and in yet another aspect from about 20 to about 350 mg of the present compound per square meter of subject body surface area. It should be recognized that these oral and parenteral dosage ranges represent generally preferred dosage ranges, and are not intended to limit the invention. The dosage regimen actually employed can vary widely, and, therefore, can deviate from the generally preferred dosage regimen. It is contemplated that one skilled in the art will tailor these ranges to the individual subject.

Toxicity and therapeutic efficacy of such compounds and bioconjugates can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds and bioconjugates that exhibit large therapeutic indices are preferred. While compounds and bioconjugates exhibiting toxic side effects can be used, care should be taken to design a delivery system that targets such compounds and bioconjugates to the site affected by the disease or disorder in order to minimize potential damage to unaffected cells and reduce side effects.

Data obtained from the cell culture assays and animal studies can be used in formulating a range of dosages for use in humans and other mammals. The dosage of such compounds and bioconjugates lies preferably within a range of circulating plasma or other bodily fluid concentrations that include the $ED_{50}$ and provides clinically efficacious results (i.e., reduction in disease symptoms). The dosage can vary within this range depending upon the dosage form employed and the route of administration utilized. For any compound and bioconjugate of the present invention, the therapeutically effective amount can be estimated initially from cell culture assays. A dosage can be formulated in animal models to achieve a circulating plasma concentration range that includes the $ED_{50}$ (the concentration of the test compound that achieves a half-maximal inhibition of symptoms) as determined in cell culture. Such information can be used to more accurately determine useful dosages in humans and other mammals. Compound and bioconjugate levels in plasma can be measured, for example, by high performance liquid chromatography.

An amount of a compound or bioconjugate that can be combined with a pharmaceutically acceptable carrier to produce a single dosage form will vary depending upon the patient treated and the particular mode of administration. It will be appreciated by those skilled in the art that the unit content of a compound/bioconjugate contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage and dosage regime for treating a disease or condition can be selected in accordance with a variety of factors, including the type, age, weight, sex, diet and/or medical condition of the patient, the route of administration, pharmacological considerations such as activity, efficacy, pharmacokinetic and/or toxicology profiles of the particular compound/bioconjugate employed, whether a compound/bioconjugate delivery system is utilized, and/or whether the compound/bioconjugate is administered as a pro-drug or part of a drug combination. Thus, the dosage regime actually employed can vary widely from subject to subject, or disease to disease and different routes of administration can be employed in different clinical settings.

The identified compounds/bioconjugates monitor, treat, inhibit, control and/or prevent, or at least partially arrest or partially prevent, diseases and conditions of interest and can be administered to a subject at therapeutically effective amounts and optionally diagnostically effective amounts. Compositions/formulations of the present invention comprise a therapeutically effective amount (which can optionally include a diagnostically effective amount) of at least one compound or bioconjugate of the present invention. Subjects receiving treatment that includes a compound/bioconjugate of the invention are preferably animals (e.g., mammals, reptiles and/or avians), more preferably humans, horses, cows, dogs, cats, sheep, pigs, and/or chickens, and most preferably humans.

Administration: The preferred composition depends on the route of administration. Any route of administration can be used as long as the target of the compound or pharmaceutically acceptable salt is available via that route. Suitable routes of administration include, for example, oral, intravenous, parenteral, inhalation, rectal, nasal, topical (e.g., transdermal and intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration.

In an embodiment, the invention provides a method for treating a medical condition comprising administering to a subject (e.g. patient) in need thereof, a therapeutically effective amount of a composition of the invention, such as an acetylcholinesterase inhibitor composition. In an embodiment, the invention provides a method for diagnosing or aiding in the diagnosis of a medical condition comprising administering to a subject in need thereof, a diagnostically effective amount of a composition of the invention. In an embodiment, the medical condition is a skin condition or dermatological diseases.

The diagnostic and therapeutic formulations of this invention can be administered alone, but can be administered with a pharmaceutical carrier selected upon the basis of the chosen route of administration and standard pharmaceutical practice.

Any suitable form of administration can be employed in connection with the diagnostic and therapeutic formulations of the invention. The diagnostic and therapeutic formulations of this invention can be administered intravenously, in oral dosage forms, intraperitoneally, subcutaneously, or intramuscularly, all using dosage forms well known to those of ordinary skill in the pharmaceutical arts.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations can also include aerosol formulation, creams, gels, solutions, etc. The present compositions, preparations and formulations are administered in doses effective to achieve the desired diagnostic and/or therapeutic effect. Such doses can vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations can also optionally include stabilizing agents and skin penetration enhancing agents.

(i) Parenteral Administration:

Compounds and bioconjugates of the present invention can be formulated for parenteral administration by injection (e.g., by bolus injection or continuous infusion). Formulations for injection can be presented in unit dosage form in ampoules or in multi-dose containers with an optional preservative added. The parenteral preparation can be enclosed in ampoules, disposable syringes or multiple dose vials made of glass, plastic or the like. The formulation can take such forms as suspensions, solutions or emulsions in oily or aqueous vehicles, and can contain formulatory agents such as suspending, stabilizing and/or dispersing agents.

For example, a parenteral preparation can be a sterile injectable solution or suspension in a nontoxic parenterally acceptable diluent or solvent (e.g., as a solution in 1,3-butanediol). Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid can be used in the parenteral preparation.

Alternatively, compounds and bioconjugates of the present invention can be formulated in powder form for constitution with a suitable vehicle, such as sterile pyrogen-free water, before use. For example, a compound/bioconjugate suitable for parenteral administration can include a sterile isotonic saline solution containing between 0.1 percent and 90 percent weight per volume of the compound/bioconjugate. By way of example, a solution can contain from about 5 percent to about 20 percent, more preferably from about 5 percent to about 17 percent, more preferably from about 8 to about 14 percent, and still more preferably about 10 percent weight per volume of the compound/bioconjugate. The solution or powder preparation can also include a solubilizing agent and a local anesthetic such as lignocaine to ease pain at the site of the injection. Other methods of parenteral delivery of compounds/bioconjugates will be known to the skilled artisan and are within the scope of the invention.

(ii) Oral Administration:

For oral administration, a compound/bioconjugate of the invention can be formulated to take the form of tablets or capsules prepared by conventional means with one or more pharmaceutically acceptable carriers (e.g., excipients such as binding agents, fillers, lubricants and disintegrants).

(iii) Controlled-Release Administration:

Controlled-release (or sustained-release) preparations can be formulated to extend the activity of a compound/bioconjugate and reduce dosage frequency. Controlled-release preparations can also be used to effect the time of onset of action or other characteristics, such as blood levels of the compound/bioconjugate, and consequently affect the occurrence of side effects.

Controlled-release preparations can be designed to initially release an amount of a compound/bioconjugate that produces the desired therapeutic effect, and gradually and continually release other amounts of the compound/bioconjugate to maintain the level of therapeutic effect over an extended period of time. In order to maintain a near-constant level of a compound/bioconjugate in the body, the compound/bioconjugate can be released from the dosage form at a rate that will replace the amount of compound/bioconjugate being metabolized and/or excreted from the body. The controlled-release of a compound/bioconjugate can be stimulated by various inducers, e.g., change in pH, change in temperature, enzymes, water, and/or other physiological conditions or molecules.

Controlled-release systems can include, for example, an infusion pump which can be used to administer the compound/bioconjugate in a manner similar to that used for delivering insulin or chemotherapy to the body generally, or to specific organs or tumors. Typically, using such a system, the compound/bioconjugate is administered in combination with a biodegradable, biocompatible polymeric implant that releases the compound/bioconjugate over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target (e.g., organ, tissue, or group of cells), thus requiring only a fraction of a systemic dosage.

Compounds/bioconjugates of the invention can be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds/bioconjugates will be known to the skilled artisan and are within the scope of the invention.

(iv) Inhalation Administration:

Compounds/bioconjugates of the invention can be administered directly to the lung of a patient/subject by inhalation. For administration by inhalation, a compound/bioconjugate can be conveniently delivered to the lung by a number of different devices. For example, a Metered Dose Inhaler ("MDI") which utilizes canisters that contain a suitable low boiling point propellant, e.g., dichlorodifluoromethane, trichlorofluoromethane, dichlorotetrafluoroethane, carbon dioxide or other suitable gas can be used to deliver a compound/bioconjugate directly to the lung. MDI devices are available from a number of suppliers such as 3M Corporation, Aventis, Boehringer Ingleheim, Forest Laboratories, GlaxoSmithKline, Merck & Co. and Vectura.

Alternatively, a Dry Powder Inhaler (DPI) device can be used to administer a compound/bioconjugate to the lung. DPI devices typically use a mechanism such as a burst of gas to create a cloud of dry powder inside a container, which can then be inhaled by the patient. DPI devices are also well known in the art and can be purchased from a number of vendors which include, for example, GlaxoSmithKline, Nektar Therapeutics, Innovata and Vectura. A popular variation is the multiple dose DPI ("MDDPI") system, which allows for the delivery of more than one therapeutic dose. MDDPI devices are available from companies such as AstraZeneca, GlaxoSmithKline, TEVA, Merck & Co., SkyePharma and Vectura. For example, capsules and cartridges of gelatin for use in an inhaler or insufflator can be formulated containing a powder mix of the compound/bioconjugate and a suitable powder base such as lactose or starch for these systems.

Another type of device that can be used to deliver a compound/bioconjugate to the lung is a liquid spray device supplied, for example, by Aradigm Corporation. Liquid spray systems use extremely small nozzle holes to aerosolize liquid compound/bioconjugate formulations that can then be directly inhaled into the lung. For example, a nebulizer device can be used to deliver a compound/bioconjugate to the lung. Nebulizers create aerosols from liquid compound/bioconjugate formulations by using, for example, ultrasonic energy to form fine particles that can be readily inhaled. Examples of nebulizers include devices supplied by Aventis and Battelle.

In another example, an electrohydrodynamic ("EHD") aerosol device can be used to deliver a compound/bioconjugate to the lung. EHD aerosol devices use electrical energy to aerosolize liquid compound/bioconjugate solutions or suspensions. The electrochemical properties of the compound/bioconjugate formulation are important parameters to optimize when delivering this compound/bioconjugate to the lung with an EHD aerosol device. Such optimization is routinely performed by one of skill in the art. Other methods of intra-pulmonary delivery of compounds/bioconjugates will be known to the skilled artisan and are within the scope of the invention.

Liquid compound/bioconjugate formulations suitable for use with nebulizers and liquid spray devices and EHD aerosol devices will typically include the compound/bioconjugate with a pharmaceutically acceptable carrier. In one exemplary embodiment, the pharmaceutically acceptable carrier is a liquid such as alcohol, water, polyethylene glycol or a perfluorocarbon. Optionally, another material can be added to alter the aerosol properties of the solution or suspension of the compound/bioconjugate. For example, this material can be a liquid such as an alcohol, glycol, polyglycol or a fatty acid. Other methods of formulating liquid compound/bioconjugate solutions or suspensions suitable for use in aerosol devices are known to those of skill in the art.

(v) Depot Administration:

A compound/bioconjugate of the invention can be formulated as a depot preparation. Such long-acting formulations can be administered by implantation (e.g., subcutaneously or intramuscularly) or by intramuscular injection. Accordingly, the compound/bioconjugate can be formulated with suitable polymeric or hydrophobic materials such as an emulsion in an acceptable oil or ion exchange resin, or as sparingly soluble derivatives such as a sparingly soluble salt. Other methods of depot delivery of compounds/bioconjugates will be known to the skilled artisan and are within the scope of the invention.

(vi) Topical Administration:

For topical application, a compound/bioconjugate can be combined with a pharmaceutically acceptable carrier so that an effective dosage is delivered, based on the desired activity ranging from an effective dosage, for example, of 1.0 µM to 1.0 mM. In one aspect of the invention, a topical formulation of a compound/bioconjugate can be applied to the skin. The pharmaceutically acceptable carrier can be in the form of, for example, and not by way of limitation, an ointment, cream, gel, paste, foam, aerosol, suppository, pad or gelled stick.

A topical formulation can include a therapeutically effective amount of a compound/bioconjugate in an ophthalmologically acceptable excipient such as buffered saline, mineral oil, vegetable oils such as corn or *arachis* oil, petroleum jelly, Miglyol 182, alcohol solutions, or liposomes or liposome-like products. Any of these formulations of such compounds/bioconjugates can include preservatives, antioxidants, antibiotics, immunosuppressants, and other biologically or pharmaceutically effective agents that do not exert a significant detrimental effect on the compound/bioconjugate. Other methods of topical delivery of compounds/bioconjugates will be known to the skilled artisan and are within the scope of the invention. Topical formulations of the invention further include those comprising one or more compositions useful for penetrating the skin, such as dimethyl sulfoxide (DMSO).

(vii) Rectal Administration:

Compounds/bioconjugates of the invention can be formulated in rectal formulations such as suppositories or retention enemas that include conventional suppository bases such as cocoa butter or other glycerides and/or binders and/or carriers such as triglycerides, microcrystalline cellulose, gum tragacanth or gelatin. Rectal formulations can contain a compound/bioconjugate in the range of 0.5% to 10% by weight, for example. Other methods of rectal delivery of compounds/bioconjugates will be known to the skilled artisan and are within the scope of the invention.

(viii) Other Systems of Administration:

Various other delivery systems are known in the art and can be used to administer the compounds/bioconjugates of the invention. Moreover, these and other delivery systems can be combined and/or modified to promote optimization of the administration of compounds/bioconjugates of the present invention. Exemplary formulations that include compounds/bioconjugates of the present invention are described elsewhere herein (the compounds/bioconjugates of the present invention are indicated as the active ingredient, but those of skill in the art will recognize that pro-drugs and compound combinations are also meant to be encompassed by this term).

5.d: Formulation: In an embodiment, the invention provides a medicament which comprises a therapeutically effective amount of one or more compositions of the invention, such as an acetylcholinesterase inhibitor compound. In an embodiment, the invention provides a medicament which comprises a diagnostically effective amount of one or more compositions of the invention. In an embodiment, the invention provides a method for making a medicament for treatment of a condition described herein, such as the treatment of a skin condition or dermatological disease. In an embodiment, the invention provides a method for making a medicament for diagnosis or aiding in the diagnosis of a condition described herein, such as the diagnosis of a skin condition or dermatological disease. In an embodiment, the invention provides the use of one or more compositions set forth herein for the making of a medicament for the treatment of a skin condition or dermatological disease. In an embodiment, the invention provides the use of one or more compositions set forth herein for the treatment of a disease. In an embodiment, the invention provides the use of one or more compositions set forth herein for the diagnosis of a disease. Compositions of the invention include formulations and preparations comprising one or more of the present acetylcholinesterase inhibitor provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

In an embodiment, the invention provides a pharmaceutical formulation having an active ingredient comprising a composition of the invention, such as an acetylcholinesterase inhibitor compound. In an embodiment, the invention provides a method of synthesizing a composition of the invention or a pharmaceutical formulation thereof, such as an acetylcholinesterase inhibitor compound. In an embodiment, a pharmaceutical formulation comprises one or more excipients, carriers, diluents, and/or other components as would be understood in the art. Preferably, the components meet the standards of the National Formulary ("NF"), United States Pharmacopoeia ("USP"; United States Pharmacopeial Convention Inc., Rockville, Md.), or Handbook of Pharmaceutical Manufacturing Formulations (Sarfaraz K. Niazi, all volumes, ISBN: 9780849317521, ISBN 10: 0849317525; CRC Press, 2004). See, e.g., United States Pharmacopeia and National Formulary (USP 30-NF 25), Rockville, Md.: United States Pharmacopeial Convention (2007 and 2008), and each of any earlier editions; The Handbook of Pharmaceutical Excipients, published jointly by the American Pharmacists Association and the Pharmaceutical Press (Pharmaceutical Press (2005) (ISBN-10: 0853696187, ISBN-13: 978-0853696186)); Merck Index, Merck & Co., Rahway, N.J.; and Gilman et al., (eds) (1996); Goodman and Gilman's: The Pharmacological Bases of Therapeutics, 8th Ed., Pergamon Press. In embodiments, the formulation base of the formulations of the invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopeias (e.g. DAB, Ph. Eur., BP, NF, USP), as well as other excipients whose properties do not impair a physiological use.

This invention also is directed, in part, to pharmaceutical compositions including a therapeutically effective amount of a compound or salt of this invention, as well as processes for making such compositions. Such compositions generally include one or more pharmaceutically acceptable carriers (e.g., excipients, vehicles, auxiliaries, adjuvants, diluents) and can include other active ingredients. Formulation of these compositions can be achieved by various methods known in the art. A general discussion of these methods can be found in, for example, Hoover, John E., Remington's Pharmaceutical Sciences (Mack Publishing Co., Easton, Pa.: 1975). See also, Lachman, L., eds., Pharmaceutical Dosage Forms (Marcel Decker, New York, N.Y., 1980).

The diagnostic and therapeutic formulations of this invention and medicaments of this invention can further comprise one or more pharmaceutically acceptable carriers, excipients, buffers, emulsifiers, surfactants, electrolytes or diluents. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985).

Compositions of the invention include formulations and preparations comprising one or more of the present compounds provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

Compounds and bioconjugates of the present invention can be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. An individual compound/bioconjugate can be administered in combination with one or more additional compounds/bioconjugates of the present invention and/or together with other biologically active or biologically inert agents. Such biologically active or inert agents can be in fluid or mechanical communication with the compound(s)/bioconjugate(s) or attached to the compound(s)/bioconjugate(s) by ionic, covalent, Van der Waals, hydrophobic, hydrophilic or other physical forces. It is preferred that administration is localized in a subject, but administration can also be systemic.

Compounds and bioconjugates of the present invention can be formulated by any conventional manner using one or more pharmaceutically acceptable carriers. Thus, the compound(s)/bioconjugate(s) and their pharmaceutically acceptable salts and solvates can be specifically formulated for administration, e.g., by inhalation or insufflation (either through the mouth or the nose) or oral, buccal, parenteral or rectal administration. The compounds/bioconjugates can take the form of charged, neutral and/or other pharmaceutically acceptable salt forms. Examples of pharmaceutically acceptable carriers include, but are not limited to, those described in REMINGTON'S PHARMACEUTICAL SCIENCES (A. R. Gennaro, Ed.), 20th edition, Williams & Wilkins PA, USA (2000).

Compounds and bioconjugates of the present invention can be formulated in the form of solutions, suspensions, emulsions, tablets, pills, capsules, powders, controlled- or sustained-release formulations and the like. Such formulations will contain a therapeutically effective amount of the compound/bioconjugate, preferably in purified form, together with a suitable amount of carrier so as to provide the form for proper administration to the patient. The formulation should suit the mode of administration.

Pharmaceutically acceptable carriers that can be used in conjunction with the compounds of the invention are well known to those of ordinary skill in the art. Carriers can be selected based on a number of factors including, for example, the particular compound(s) or pharmaceutically acceptable salt(s) used; the compound's concentration, stability, and intended bioavailability; the condition being treated; the subject's age, size, and general condition; the route of administration; etc. A general discussion related to carriers can be found in, for example, J. G. Nairn, Remington's Pharmaceutical Science, pp. 1492-1517 (A. Gennaro, ed., Mack Publishing Co., Easton, Pa. (1985)).

Solid dosage forms for oral administration include, for example, capsules, tablets, gel-caps, pills, dragees, troches, powders, granules, and lozenges. In such solid dosage forms, the compounds or pharmaceutically acceptable salts thereof can be combined with one or more pharmaceutically acceptable carriers. The compounds and pharmaceutically acceptable salts thereof can be mixed with carriers including, but not limited to, lactose, sucrose, starch powder, corn starch, potato starch, magnesium carbonate, microcrystalline cellulose, cellulose esters of alkanoic acids, cellulose alkyl esters, talc, stearic acid, magnesium stearate, magnesium oxide, sodium and calcium salts of phosphoric and sulfuric acids, sodium carbonate, agar, mannitol, sorbitol, sodium saccharin, gelatin, acacia gum, alginic acid, sodium alginate, tragacanth, colloidal silicon dioxide, croscarmellose sodium, polyvinylpyrrolidone, and/or polyvinyl alcohol, and then tableted or encapsulated for convenient administration. Such capsules or tablets can contain a controlled-release formulation, as can be provided in a dispersion of the compound or salt in hydroxypropylmethyl cellulose. In the case of capsules, tablets, and pills, the dosage forms also can include buffering agents, such as sodium citrate, or magnesium or calcium carbonate or bicarbonate. Tablets and pills additionally can, for example, include a coating (e.g., an enteric coating) to delay disintegration and absorption. The concentration of the present compounds in a solid oral dosage form can be from about 5 to about 50% for example, and in certain aspects from about 8 to about 40%, and in another aspect from about 10 to about 30% by weight based on the total weight of the composition.

Liquid dosage forms of the compounds of the invention for oral administration include, for example, pharmaceutically acceptable emulsions, solutions, suspensions, syrups, and elixirs containing inert diluents commonly used in the art (e.g., water). Such compositions also can include adjuvants, such as wetting, emulsifying, suspending, flavoring (e.g., sweetening), and/or perfuming agents. The concentration of the present compounds in the liquid dosage form can be from about 0.01 to about 5 mg, and in certain aspects from about 0.01 to about 1 mg, and in another aspect from about 0.01 to about 0.5 mg per ml of the composition. Low concentrations of the compounds of the invention in liquid dosage form can be prepared in the case that the compound is more soluble at low concentrations. Techniques for making oral dosage forms useful in the invention are generally described in, for example, Modern Pharmaceutics, Chapters 9 and 10 (Banker & Rhodes, Editors (1979)). See also, Lieberman et al., Pharmaceutical Dosage Forms: Tablets (1981). See also, Ansel, Introduction to Pharmaceutical Dosage Forms (2nd Edition (1976)).

In some aspects of the invention, tablets or powders for oral administration can be prepared by dissolving the compound in a pharmaceutically acceptable solvent capable of dissolving the compound to form a solution and then evaporating when the solution is dried under vacuum. A carrier can also be added to the solution before drying. The resulting solution can be dried under vacuum to form a glass. The glass can then be mixed with a binder to form a powder. This powder can be mixed with fillers or other conventional tableting agents, and then processed to form a tablet. Alternatively, the powder can be added to a liquid carrier to form a solution, emulsion, suspension, or the like.

In some aspects, solutions for oral administration are prepared by dissolving the compound in a pharmaceutically acceptable solvent capable of dissolving the compound to form a solution. An appropriate volume of a carrier is added to the solution while stirring to form a pharmaceutically acceptable solution for oral administration.

In some embodiments, a liposome or micelle can be utilized as a carrier or vehicle for the composition. For example, in some embodiments, the compound can be a part of the lipophilic bilayers or micelle, and the targeting ligand, if present, can be on the external surface of the liposome or micelle. As another example, a targeting ligand can be externally attached to the liposome or micelle after formulation for targeting the liposome or micelle (which contains the acetylcholinesterase inhibitor agents) to the desired tissue, organ, or other site in the body.

Injectable preparations (e.g., sterile injectable aqueous or oleaginous suspensions) can be formulated according to the known art using suitable dispersing, wetting agents, and/or suspending agents. Acceptable vehicles for parenteral use include both aqueous and nonaqueous pharmaceutically-acceptable solvents. Suitable pharmaceutically acceptable aqueous solvents include, for example, water, saline solutions, dextrose solutions (such as DW5), electrolyte solutions, etc.

In one embodiment, the present compounds are formulated as nanoparticles or microparticles. Use of such nanoparticle or microparticle formulations can be beneficial for some applications to enhance delivery, localization, target specificity, administration, etc. of the compound. Potentially useful nanoparticles and microparticles include, but are not limited to, micelles, liposomes, microemulsions, nanoemulsions, vesicles, tubular micelles, cylindrical micelles, bilayers, folded sheets structures, globular aggregates, swollen micelles, inclusion complex, encapsulated droplets, microcapsules, nanocapsules or the like. As will be understood by those having skill in the art, the present compounds can be located inside the nanoparticle or microparticle, within a membrane or wall of the nanoparticle or microparticle, or outside of (but bonded to or otherwise associated with) the nanoparticle or microparticle. The agent formulated in nanoparticles or microparticles can be administered by any of the routes previously described. In a formulation applied topically, the compound is slowly released over time. In an injectable formulation, the liposome, micelle, capsule, etc., circulates in the bloodstream and is delivered to the desired site (e.g., target tissue).

Preparation and loading of nanoparticles and microparticles are well known in the art. As one example, liposomes can be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, Liposome Dermatics, Springer-Verlag, Berlin (1992), pp. 69 81; 91 117. Polycaprolactone, poly(glycolic) acid, poly(lactic) acid, polyanhydride or lipids can be formulated as microspheres. As an illustrative example, the present compounds can be mixed with polyvinyl alcohol (PVA), the mixture then dried and coated with ethylene vinyl acetate, then cooled again with PVA. In a liposome, the present compounds can be within one or both lipid bilayers, in the aqueous between the bilayers, or within the center or core. Liposomes can be modified with other molecules and lipids to form a cationic liposome. Liposomes can also be modified with lipids to render their surface more hydrophilic which increases their circulation time in the bloodstream. The thus-modified liposome has been termed a "stealth" liposome, or a long-lived liposome, as described in U.S. Pat. No. 6,258,378, and in Stealth Liposomes, Lasic and Martin (Eds.) 1995 CRC Press, London. Encapsulation methods include detergent dialysis, freeze drying, film forming, injection, as known to one skilled in the art and disclosed in, for example, U.S. Pat. No. 6,406,713. Optionally, the present compositions and methods include a micelle delivery system, for example, involving one or more PEG-based amphiphilic polymers developed for drug delivery including: PEG-poly(-caprolactone), PEG-poly(amino acid), PEG-polylactide or PEG-phospholipid constructs; a cross linked poly(acrylic acid) polymer system, a phospholipid-based system and/or block copolymer systems comprising one or more of the following polymer blocks: a poly(lactic acid) polymer block; a poly(propylene glycol) polymer block; a poly(amino acid) polymer block; a poly(ester) polymer block; a poly (-caprolactone) polymer block; a poly(ethylene glycol) block, a poly(acrylic acid) block; a polylactide block; a polyester block; a polyamide block; a polyanhydride block; a polyurethane block; a polyimine block; a polyurea block; a polyacetal block; a polysaccharide block; and a polysiloxane block.

Suitable pharmaceutically-acceptable nonaqueous solvents include, but are not limited to, the following (as well as mixtures thereof):

(i) Alcohols (these include, for example, α-glycerol formal, β-glycerol formal, 1, 3-butyleneglycol, aliphatic or aromatic alcohols having from 2 to about 30 carbons (e.g., methanol, ethanol, propanol, isopropanol, butanol, t-butanol, hexanol, octanol, amylene hydrate, benzyl alcohol, glycerin (glycerol), glycol, hexylene, glycol, tetrahydrofuranyl alcohol, cetyl alcohol, and stearyl alcohol), fatty acid esters of fatty alcohols (e.g., polyalkylene glycols, such as polypropylene glycol and polyethylene glycol), sorbitan, sucrose, and cholesterol);

(ii) Amides, which include, for example, dimethylacetamide (DMA), benzyl benzoate DMA, dimethylformamide, N-hydroxyethyO-lactamide, N, N-dimethylacetamide-amides, 2-pyrrolidinone, 1-methyl-2-pyrrolidinone, and polyvinylpyrrolidone;

(iii) Esters, which include, for example, acetate esters (e.g., monoacetin, diacetin, and triacetin), aliphatic and aromatic esters (e.g., ethyl caprylate or octanoate, alkyl oleate, benzyl benzoate, or benzyl acetate), dimethylsulfoxide (DMSO), esters of glycerin (e.g., mono, di, and triglyceryl citrates and tartrates), ethyl benzoate, ethyl acetate, ethyl carbonate, ethyl lactate, ethyl oleate, fatty acid esters of sorbitan, glyceryl monostearate, glyceride esters (e.g., mono, di, or tri-glycerides), fatty acid esters (e.g., isopropyl myristrate), fatty acid derived PEG esters (e.g., PEG-hydroxyoleate and PEG-hydroxystearate), N-methyl pyrrolidinone, pluronic 60, polyoxyethylene sorbitol oleic polyesters (e.g., poly(ethoxylated)$_{30-60}$ sorbitol poly(oleate)$_{2-4}$, poly (oxyethylene)$_{15-20}$ monooleate, poly(oxyethylene)$_{15-20}$ mono 12-hydroxystearate, and poly(oxyethylene)$_{15-20}$ mono ricinoleate), polyoxyethylene sorbitan esters (e.g., polyoxyethylene-sorbitan monooleate, polyoxyethylene-sorbitan monopalmitate, polyoxyethylene-sorbitan monolaurate, polyoxyethylene-sorbitan monostearate, and POLYSORBATE 20, 40, 60, and 80 (from ICI Americas, Wilmington, Del.)), polyvinylpyrrolidone, alkyleneoxy modified fatty acid esters (e.g., polyoxyl 40 hydrogenated castor oil and polyoxyethylated castor oils, such as CREMOPHOR EL solution or CREMOPHOR RH 40 solution), saccharide fatty acid esters (i.e., the condensation product of a monosaccharide (e.g., pentoses, such as, ribose, ribulose, arabinose, xylose, lyxose, and xylulose; hexoses, such as glucose, fructose, galactose, mannose, and sorbose; trioses; tetroses; heptoses; and octoses), disaccharide (e.g., sucrose, maltose, lactose, and trehalose), oligosaccharide, or a mixture thereof with one or more $C_4$-$C_{22}$ fatty acids (e.g., saturated fatty acids, such as caprylic acid, capric acid, lauric acid, myristic acid, palmitic acid, and stearic acid; and unsaturated fatty acids, such as palmitoleic acid, oleic acid, elaidic acid, erucic acid, and linoleic acid), and steroidal esters;

(iv) Ethers, for example, alkyl, aryl, and cyclic ethers having from 2 to about 30 carbons. Examples include diethyl ether, tetrahydrofuran, di methyl isosorbide, diethylene glycol monoethyl ether), and glycofurol (tetrahydrofurfuranyl alcohol polyethylene glycol ether);

(v) Ketones which typically have from about 3 to about 30 carbons. Examples include acetone, methyl ethyl ketone, and methyl isobutyl ketone;

(vi) Hydrocarbons which are typically aliphatic, cycloaliphatic, or aromatic hydrocarbons having from about 4 to about 30 carbons. Examples include benzene, cyclohexane, dichloromethane, dioxolanes, hexane, n-decane, n-dodecane, n-hexane, sulfolane, tetramethylenesulfone, tetramethylenesulfoxide, toluene, di methylsulfoxide (DMSO); and tetramethylene sulfoxide;

(vii) Oils which include, for example, oils of mineral, vegetable, animal, essential, or synthetic origin. These include: mineral oils, such as aliphatic and wax-based hydrocarbons, aromatic hydrocarbons, mixed aliphatic and aromatic based hydrocarbons, and refined paraffin oil; vegetable oils, such as linseed, tung, safflower, soybean, castor, cottonseed, groundnut, rapeseed, coconut, palm, olive, corn, corn germ, sesame, persic, and peanut oil; glycerides, such as mono-, di-, and triglycerides; animal oils, such as fish, marine, sperm, cod-liver, haliver, squaiene, squalane, and shark liver oil; oleic oils; and polyoxyethylated castor oil;

(viii) Alkyl, alkenyl, or aryl halides which include, for example, alkyl or aryl halides having from 1 to about 30 carbons and one or more halogen substituents. Examples include: methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (SOLUTOL HS-15, from BASF, Ludwigshafen, Germany); polyoxyethylene glycerol; sodium laurate; sodium oleate; and sorbitan monooleate.

Other pharmaceutically acceptable solvents for use in the invention are well known to those of ordinary skill in the art. General discussion relating to such solvents can be found in, for example, The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics 3d ed., (G. Banker et. al., eds., Marcel Dekker, Inc., New York, N.Y. (1995)), The Pharmacological Basis of Therapeutics, (Goodman & Gilman, McGraw Hill Publishing), Pharmaceutical Dosage Forms, (H. Lieberman et. al., eds., Marcel Dekker, Inc., New York, N.Y. (1980)), Remington's Pharmaceutical Sciences, 19th ed., (A. Gennaro, ed., Mack Publishing, Easton, Pa., (1995)), The United States Pharmacopeia 24, The National Formulary 19, (National Publishing, Philadelphia, Pa. (2000)); Spiegel, A. J., et al., "Use of Nonaqueous Solvents in Parenteral Products," J. Pharma. Sciences, Vol. 52, No. 10, pp. 917-927 (1963).

Solvents useful in the invention include, but are not limited to, those known to stabilize present compounds or pharmaceutically acceptable salts thereof. These can include, for example, oils rich in triglycerides, such as safflower oil, soybean oil, and mixtures thereof; and alkyleneoxy-modified fatty acid esters, such as polyoxyl 40 hydrogenated castor oil and polyoxyethylated castor oils (e.g., CREMOPHOR EL solution or CREMOPHOR RH 40 solution). Commercially available triglycerides include INTRALIPID emulsified soybean oil (Kabi-Pharmacia Inc., Stockholm, Sweden), NUTRALIPID emulsion (McGaw, Irvine, Calif.), LIPOSYN II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), LIPOSYN III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels of from about 25 to about 100% (by weight based on the total fatty acid content) (DHASCO from Martek Biosciences Corp., Columbia, Md.; DHA MAGURO from Daito Enterprises, Los Angeles, Calif.; SOYACAL; and TRAVEMULSION). Ethanol in particular is a useful solvent for dissolving a compound or pharmaceutically acceptable salt thereof to form solutions, emulsions, and the like.

Additional components can be included in the compositions of this invention for various purposes generally known in the pharmaceutical industry. These components tend to impart properties that, for example, enhance retention of the present compounds or salt thereof at the site of administration, protect the stability of the composition, control the pH, and facilitate processing of the compound or salt thereof into pharmaceutical formulations, and the like. Specific examples of such components include cryoprotective agents; agents for preventing reprecipitation of the compound or salt surface; active, wetting, or emulsifying agents (e.g., lecithin, polysorbate-80, TWEEN 80, pluronic 60, and polyoxyethylene stearate); preservatives (e.g., ethyl-p-hydroxybenzoate); microbial preservatives (e.g., benzyl alcohol, phenol, m-cresol, chlorobutanol, sorbic acid, thimerosal, and paraben); agents for adjusting pH or buffering agents (e.g., acids, bases, sodium acetate, sorbitan monolaurate, etc.); agents for adjusting osmolarity (e.g., glycerin); thickeners (e.g., aluminum monostearate, stearic acid, cetyl alcohol, stearyl alcohol, guar gum, methyl cellulose, hydroxypropylcellulose, tristearin, cetyl wax esters, polyethylene glycol, etc.); colorants; dyes; flow aids; non-volatile silicones (e.g., cyclomethicone); clays (e.g., bentonites); adhesives; bulking agents; flavorings; sweeteners; adsorbents; fillers (e.g., sugars such as lactose, sucrose, mannitol, sorbitol, cellulose, calcium phosphate, etc.); diluents (e.g., water, saline, electrolyte solutions, etc.); binders (e.g., gelatin; gum tragacanth; methyl cellulose; hydroxypropyl methylcellulose; sodium carboxymethyl cellulose; polyvinylpyrrolidone; sugars; polymers; acacia; starches, such as maize starch, wheat starch, rice starch, and potato starch; etc.); disintegrating agents (e.g., starches, such as maize starch, wheat starch, rice starch, potato starch, and carboxymethyl starch; cross-linked polyvinyl pyrrolidone; agar; alginic acid or a salt thereof, such as sodium alginate; croscarmellose sodium; crospovidone; etc); lubricants (e.g., silica; talc; stearic acid and salts thereof, such as magnesium stearate; polyethylene glycol; etc.); coating agents (e.g., concentrated sugar solutions including gum arabic, talc, polyvinyl pyrrolidone, carbopol gel, polyethylene glycol, titanium dioxide, etc.); and antioxidants (e.g., sodium metabisulfite, sodium bisulfite, sodium sulfite, dextrose, phenols, thiophenols, etc.).

Techniques and compositions for making parenteral dosage forms are generally known in the art. Formulations for parenteral administration can be prepared from one or more sterile powders and/or granules having a compound or salt of this invention and one or more of the carriers or diluents mentioned for use in the formulations for oral administration. The powder or granule typically is added to an appropriate volume of a solvent (typically while agitating (e.g., stirring) the solvent) that is capable of dissolving the powder or granule. Particular solvents useful in the invention include, for example, water, polyethylene glycol, propylene glycol, ethanol, corn oil, cottonseed oil, peanut oil, sesame oil, benzyl alcohol, sodium chloride, and/or various buffers.

Emulsions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the emulsion. Solutions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the solution.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, cocoa butter; synthetic mono-, di-, or triglycerides; fatty acids; and/or polyethylene glycols.

Every formulation or combination of components described or exemplified herein can be used to practice the invention, unless otherwise stated.

(i) Binding Agents:

Binding agents include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof. Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., USA). An exemplary suitable binder is a mixture of microcrystalline cellulose and sodium carboxymethyl cellulose sold as AVICEL RC-581 by FMC Corporation.

(ii) Fillers:

Fillers include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, and mixtures thereof.

(iii) Lubricants:

Lubricants include, but are not limited to, calcium stearate, magnesium stearate, mineral oil, electromagnetic radiation mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md., USA), a coagulated aerosol of synthetic silica (marketed by Deaussa Co. of Plano, Tex., USA), CAB-O-SIL (a pyrogenic silicon dioxide product sold by Cabot Co. of Boston, Mass., USA), and mixtures thereof.

(iv) Disintegrants:

Disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Tablets or capsules can optionally be coated by methods well known in the art. If binders and/or fillers are used with a compound/bioconjugate of the invention, they are typically formulated as about 50 to about 99 weight percent of the compound/bioconjugate. In one aspect, about 0.5 to about 15 weight percent of disintegrant, and particularly about 1 to about 5 weight percent of disintegrant, can be used in combination with the compound. A lubricant can optionally be added, typically in an amount of less than about 1 weight percent of the compound/bioconjugate. Techniques and pharmaceutically acceptable additives for making solid oral dosage forms are described in Marshall, SOLID ORAL DOSAGE FORMS, Modern Pharmaceutics (Banker and Rhodes, Eds.), 7:359-427 (1979). Other formulations are known in the art.

Liquid preparations for oral administration can take the form of solutions, syrups or suspensions. Alternatively, the liquid preparations can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations can also contain buffer salts, flavoring, coloring, perfuming and sweetening agents as appropriate. Preparations for oral administration can also be formulated to achieve controlled release of the compound/bioconjugate. Oral formulations preferably contain 10% to 95% compound/bioconjugate. In addition, a compound/bioconjugate of the present invention can be formulated for buccal administration in the form of tablets or lozenges formulated in a conventional manner. Other methods of oral delivery of compounds/bioconjugates of the invention will be known to the skilled artisan and are within the scope of the invention.

Formulation 1:

Hard gelatin capsules prepared using the following:

TABLE F1

| Ingredients | (mg/capsule) |
| --- | --- |
| Active Ingredient | 250.0 |
| Starch | 305.0 |
| Magnesium stearate | 5.0 |

The ingredients are mixed and filled into hard gelatin capsules in 560 mg quantities.

Formulation 2:

A tablet formula is prepared using the following ingredients:

TABLE F2

| Ingredients | (mg/tablet) |
| --- | --- |
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each 665 mg.

Formulation 3:

A dry powder inhaler formulation is prepared containing the following components:

TABLE F3

| Ingredients | Weight % |
| --- | --- |
| Active ingredient | 5 |
| Lactose | 95 |

The active ingredient is mixed with the lactose and the mixture is added to a dry powder inhaling appliance.

Formulation 4:

Tablets, each containing 60 mg of active ingredient, are prepared as follows:

TABLE F4

| Ingredients | Milligrams |
| --- | --- |
| Active ingredient | 60.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 150.0 |

The active ingredient, starch and cellulose are passed through a No. 20 mesh U.S. sieve and mixed thoroughly. The solution of polyvinylpyrrolidone is mixed with the resultant powders which are then passed through a 16 mesh U.S. sieve. The granules as produced are dried at 50-60° C.

and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5:

Capsules, each containing 80 mg of active ingredient are made as follows:

TABLE F5

| Ingredients | Milligrams |
| --- | --- |
| Active ingredient | 80.0 |
| Starch | 109.0 |
| Magnesium stearate | 1.0 |
| Total | 190.0 |

The active ingredient, cellulose, starch, and magnesium stearate are blended, passed through a No. 20 mesh U.S. sieve, and filled into hard gelatin capsules in 190 mg quantities.

Formulation 6:

Suppositories, each containing 225 mg of active ingredient, are made as follows:

TABLE F6

| Ingredients | Milligrams |
| --- | --- |
| Active Ingredient | 225 |
| Saturated fatty acid glycerides to | 2000 |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7:

Suspensions, each containing 50 mg of active ingredient per 5.0 ml dose are made as follows:

TABLE F7

| Ingredients | Milligrams |
| --- | --- |
| Active ingredient | 50.0 mg |
| Xanthan gum | 4.0 mg |
| Sodium carboxymethyl cellulose | (11%) |
| Microcrystalline cellulose | (89%) |
| | 50.0 mg |
| Sucrose | 1.75 g |
| Sodium benzoate | 10.0 mg |
| Flavor | q.v. |
| Color | q.v. |
| Purified water to | 5.0 ml |

The active ingredient, sucrose and xantham gum are blended, passed through a No. 10 mesh U.S. sieve, and mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8:

Capsules, each containing 150 mg of active ingredient, are made as follows:

TABLE F8

| Ingredients | Milligrams |
| --- | --- |
| Active ingredient | 150.0 |
| Starch | 407.0 |
| Magnesium stearate | 3.0 |
| Total | 560.0 |

The active ingredient, cellulose, starch, and magnesium stearate are blended, passed through a No. 20 mesh U.S. sieve, and filled into hard gelatin capsules in 560 mg quantities.

Kits: Various embodiments of the present invention include kits. Such kits can include a compound/bioconjugate of the present invention, optionally one or more ingredients for preparing a pharmaceutically acceptable formulation of the compound/bioconjugate, and instructions for use (e.g., administration). When supplied as a kit, different components of a compound/bioconjugate formulation can be packaged in separate containers and admixed immediately before use. Such packaging of the components separately can, if desired, be presented in a pack or dispenser device which can contain one or more unit dosage forms containing the compound/bioconjugate. The pack can, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

It is further contemplated that the compounds and salts of this invention can be used in the form of a kit that is suitable for use in performing the methods described herein, packaged in a container. The kit can contain the compound or compounds and, optionally, appropriate diluents, devices or device components suitable for administration and instructions for use in accordance with the methods of the invention. The devices can include parenteral injection devices, such as syringes or transdermal patch or the like. Device components can include cartridges for use in injection devices and the like. In one aspect, the kit includes a first dosage form including a compound or salt of this invention and a second dosage form including another active ingredient in quantities sufficient to carry out the methods of the invention. The first dosage form and the second dosage form together can include a therapeutically effective amount of the compounds for treating the targeted condition(s).

In certain embodiments, kits can be supplied with instructional materials. Instructions can be printed on paper or other substrate, and/or can be supplied as an electronic-readable medium, such as a floppy disc, mini-CD-ROM, CD-ROM, DVD-ROM, Zip disc, videotape, audio tape, and the like. Detailed instructions cannot be physically associated with the kit; instead, a user can be directed to an Internet web site specified by the manufacturer or distributor of the kit, or supplied as electronic mail.

If desired, the emulsions or solutions described above for oral or parenteral administration can be packaged in IV bags, vials, or other conventional containers in concentrated form, and then diluted with a pharmaceutically acceptable liquid (e.g., saline) to form an acceptable compound concentration before use.

Kits can include reagents in separate containers such as, for example, sterile water or saline to be added to a lyophilized active component packaged separately. For example, sealed glass ampules can contain lyophilized superoxide dismutase mimetics and in a separate ampule, sterile water, sterile saline or sterile each of which has been packaged under a neutral non-reacting gas, such as nitrogen. Ampules can consist of any suitable material, such as glass, organic polymers, such as polycarbonate, polystyrene, ceramic, metal or any other material typically employed to hold reagents. Other examples of suitable containers include bottles that can be fabricated from similar substances as ampules, and envelopes that can consist of foil-lined interiors, such as aluminum or an alloy. Other containers include test tubes, vials, flasks, bottles, syringes, and the like. Containers can have a sterile access port, such as a bottle having a stopper that can be pierced by a hypodermic injection needle. Other containers can have two compartments that are separated by a readily removable membrane that upon removal permits the components to mix. Removable membranes can be glass, plastic, rubber, and the like.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference). For example, U.S. Provisional Application Nos. 61/859,572, filed Jul. 29, 2013, 61/861,072, filed Aug. 1, 2013 and 61/953,290 filed Mar. 14, 2014, U.S. nonprovisional application Ser. No. 14/444,748 filed Jul. 28, 2014 (published Mar. 26, 2015 as U.S. Pub. No. 2015/0086596A1), and PCT Application No. PCT/US14/48420 filed Jul. 28, 2014 (published Feb. 5, 2015 as Pub. No. WO 2015/017328), each of which is hereby incorporated by reference in their entireties to the extent not inconsistent herewith.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A method of treating a skin affliction associated with *Demodex brevis* and/or *Demodex folliculorum* mites comprising a step of topically-applying to an individual having the skin affliction an acetylcholinesterase inhibitor selected from the group consisting of physostigmine, demecarium, donepezil, tacrine, echothiophate, diisopropyl fluorophosphate, lactucopicrin, *boswellia, celastrus* paniculatus, coumarins, galantamine, and huperzine A, or a prodrug or pharmaceutically acceptable salt thereof, in a dosage effective to inactivate *Demodex brevis* and/or *Demodex folliculorum* mites in hair follicles and/or skin of the individual, resulting in amelioration or cessation of the manifestations of allergic and/or vasomotor responses to the mites that cause symptoms and signs of the skin affliction in the individual.

2. The method of claim 1, wherein said acetylcholinesterase inhibitor is efficiently transported into the epidermis or a subdermal region upon contact with said hair follicles and/or skin of the individual.

3. The method of claim 1, wherein said step of topically-applying said acetylcholinesterase inhibitor kills at least a portion of said *demodex brevis* and/or *demodex folliculorum* mites or renders at least a portion of said *demodex brevis* and/or *demodex folliculorum* mites unable to reproduce.

4. The method of claim 1, wherein said step of topically-applying said acetylcholinesterase inhibitor kills and eliminates said *demodex brevis* and/or *demodex folliculorum* mites.

5. The method of claim 1, wherein the skin affliction is one or more of common acne, seborrheic dermatitis, perioral dermatitis, an acneform rash, transient acantholytic dermatosis, acne necrotica milliaris, steroid induced dermatitis, primary irritation dermatitis or rosacea.

6. The method of claim 1, wherein the skin affliction affects facial skin or eyelids, or both.

7. The method of claim 1, wherein said acetylcholinesterase inhibitor is a carbamate.

8. The method of claim 7, wherein said carbamate is a miticide or insecticide.

9. The method of claim 1, wherein said acetylcholinesterase inhibitor is a naturally occurring compound.

10. The method of claim 1, wherein said acetylcholinesterase inhibitor is topically applied and the topically-applied acetylcholinesterase inhibitor is formulated in a carrier lotion, cream, soap, wash, shampoo or gel.

11. The method of claim 10, wherein a concentration of the acetylcholinesterase inhibitor in the topically-applied lotion, cream, soap, wash, shampoo or gel is a lowest concentration effective for killing the *demodex* mites.

12. The method of claim 1, wherein the topically-applied acetylcholinesterase inhibitor penetrates an outer layer of the skin of the individual, thereby exposing the *demodex brevis* and/or *demodex folliculorum* mites present below the outer layer of the skin to the acetylcholinesterase inhibitor.

13. The method of claim 12, wherein the topically-applied acetylcholinesterase inhibitor penetrates to a subdermal region of the skin of the individual, thereby exposing the *demodex brevis* and/or *demodex folliculorum* mites present in the subdermal region of the skin to the acetylcholinesterase inhibitor.

14. The method of claim 1, wherein the topically-applied acetylcholinesterase inhibitor is applied to the affected skin areas and/or to non-affected skin areas during a first application period, thereby killing and eliminating adult *demodex brevis* and/or *demodex folliculorum* mites from the hair follicles in the skin of the individual, and wherein the topically-applied acetylcholinesterase inhibitor is further applied to the affected skin areas and/or to non-affected skin areas during a second application period, thereby killing and eliminating from the hair follicles and/or skin of the individual *demodex brevis* and/or *demodex folliculorum* mites that have matured from a larval form and/or an egg form present on and/or in the skin during the first application period.

15. The method of claim 1, wherein the acetylcholinesterase inhibitor is topically-applied in a continued intermittent regime sufficient for prophylactic control of *demodex* mite population in the hair follicles and/or skin of the individual.

16. The method of claim 1, wherein the inactivation of the *demodex brevis* and/or *demodex folliculorum* mites from hair follicles and/or skin of the individual results in a reduction in population of one or more bacteria in the hair follicles and/or skin of the individual.

17. The method of claim 16, wherein the allergic and/or vasomotor responses to the mites result from a presence of one or more bacteria associated with the mites in the hair follicles and/or skin of the individual.

18. The method of claim 16, wherein the one or more bacteria comprise one or more bacteria from the genus *Staphylococcus* or from the genus *Bacillus*.

19. The method of claim 16, wherein the one or more bacteria comprise *Bacillus oleronius* bacteria.

20. The method of claim 16, wherein the one or more bacteria comprise *Staphylococcus epidermidis* bacteria.

21. The method claim 16, wherein the one or more bacteria are present in a digestive system of the *demodex brevis* and/or *demodex folliculorum* mites.

22. A method of treating a skin affliction associated with *Demodex brevis* and/or *Demodex folliculorum* mites comprising a step of topically-applying to an individual having the skin affliction an active ingredient comprising an acetylcholinesterase inhibitor selected from the group consisting of physostigmine, demecarium, donepezil, tacrine, echothiophate, diisopropyl fluorophosphates, lactucopicrin, *boswellia, celastrus* paniculatus, coumarins, galantamine, and huperzine A, or a prodrug or pharmaceutically acceptable salt thereof, in a dosage sufficient to inactivate *Demodex brevis* and/or *Demodex folliculorum* mites in hair follicles and/or skin of the individual, resulting in amelioration or cessation of the manifestations of allergic and/or vasomotor responses to the mites that cause symptoms and signs of the skin affliction in the individual, wherein the topically-applied active ingredient is applied to skin areas affected by the skin affliction and to skin areas not affected by the skin affliction.

23. The method of claim 22, wherein said active ingredient is a carbamate.

24. The method of claim 1, wherein said acetylcholinesterase inhibitor is a reversible competitive or noncompetitive inhibitor of acetylcholinesterase.

25. The method of claim 1, wherein said acetylcholinesterase inhibitor is a quasi-reversible inhibitor of acetylcholinesterase.

26. The method of claim 1, wherein said acetylcholinesterase inhibitor is Echothiophate, or Diisopropyl fluorophosphate.

27. The method of claim 1, wherein said acetylcholinesterase inhibitor is selected from the group consisting of: Huperzine A; Galantamine; and Coumarins, or a prodrug or pharmaceutically acceptable salt thereof.

28. The method of claim 1, wherein the acetylcholinesterase inhibitor has an established safety profile in humans.

29. The method of claim 22, wherein the acetylcholinesterase inhibitor has an established safety profile in humans.

* * * * *